US009678075B2

(12) United States Patent
Schröder et al.

(10) Patent No.: US 9,678,075 B2
(45) Date of Patent: Jun. 13, 2017

(54) PREDICTION OF RECURRENCE FOR BLADDER CANCER BY A PROTEIN SIGNATURE IN TISSUE SAMPLES

(75) Inventors: Christoph Schröder, Heidelberg (DE); Harish Srinivasan, Heidelberg (DE); Jörg Hoheisel, Wiesloch (DE); François Radvanyi, Paris (FR)

(73) Assignees: Deutsches Krebsforschungszentrum, Heidelberg (DE); Institut Curie, Paris (FR)

( * ) Notice: Subject to any disclaimer, the term of this patent is extended or adjusted under 35 U.S.C. 154(b) by 0 days.

(21) Appl. No.: 14/124,580

(22) PCT Filed: Jun. 8, 2012

(86) PCT No.: PCT/EP2012/060876
§ 371 (c)(1),
(2), (4) Date: Feb. 21, 2014

(87) PCT Pub. No.: WO2012/168421
PCT Pub. Date: Dec. 13, 2012

(65) Prior Publication Data
US 2014/0193927 A1     Jul. 10, 2014

(30) Foreign Application Priority Data
Jun. 10, 2011 (EP) .................................. 11169588

(51) Int. Cl.
*G01N 33/574* (2006.01)

(52) U.S. Cl.
CPC ... *G01N 33/57407* (2013.01); *G01N 2800/52* (2013.01); *G01N 2800/54* (2013.01); *G01N 2800/56* (2013.01)

(58) Field of Classification Search
CPC ......... G01N 33/57407; G01N 2800/52; G01N 2800/54; G01N 2800/56
See application file for complete search history.

(56) References Cited

U.S. PATENT DOCUMENTS

| 5,744,305 A | 4/1998 | Fodor et al. | |
| 2010/0173024 A1* | 7/2010 | McDaniel | A61K 31/05 424/729 |
| 2011/0110958 A1* | 5/2011 | Qiu | A61K 31/17 424/174.1 |

FOREIGN PATENT DOCUMENTS

| WO | WO 2006/063567 A1 | 6/2006 | |
| WO | WO 2010080933 A1 * | 7/2010 | ............... C12Q 1/68 |
| WO | WO 2011/101330 | 8/2011 | |

OTHER PUBLICATIONS

Babjuk et al., Transurethral Resection of Non-muscle-invasive Bladder Cancer, European Urology Supplements 8 (2009) 542-548.*
Etoh et al., Increased Expression of collagenase-3 (MMP-13) and MT1-MMP in oesophageal cancer is related to cancer aggressiveness, Gut 2000;47:50-56.*
Bostrom et al., Expression of Colagenase-3 (matrix metalloproteinase-13) Transitional-Cell Carcinoma of the Urinary Bladder, Int. J. Cancer: 88, 417-423 (2000).*
Schwanhausser et al., Global quantification of mammalian gene expression control, Nature, 473, 2011, 337-342.*
Faridi et al., Expression of Constitutively Active Akt-3 in MCF-7 Breast Cancer Cells Reverses the Estrogen and Tamoxifen Responsivity of these Cells in Vivo, Clin. Cancer Research, 2003, 2933-2939.*
Anderson, The Clinical Plasma Proteome: A Survey of Clinical Assays for Proteins in Plasma and Serum, Clinical Chemistry, 56:2, 177-185 (2010).*
Hall et al., Protein microarray technology, Mechanisms of Ageing and Development 128 (2007) 161-167.*
International Preliminary Report on Patentability issues in related International Patent Application No. PCT/EP2012/060876, dated Dec. 27, 2013.
Karam et al., "Use of combined apoptosis biomarkers for prediction of bladder cancer recurrence and mortality after radical cystectomy," *Lancet Oncol.*, vol. 8, pp. 128-136 (2007).
Jacobs, et al., "Bladder Cancer in 2010," *CA Cancer J. Clin.*, vol. 60, No. 4, pp. 244-272 (2010).
Mansoor et al., "Superficial Bladder Tumours: Recurrence and Progression," *J. Coll. Physicians Surg. Pak.*, vol. 21, No. 3, pp. 157-160 (2011).
Sill et al., "Assessment and Optimisation of Normalisation Methods for Dual-Colour Antibody Microarrays," *BMC Bioinfommtics*, vol. 11, pp. 556 (2010).
Tibshirani et al. "Diagnosis of Multiple Cancer Types by Shrunken Centroids of Gene Expression," *PNAS*, vol. 99, No. 10, pp. 6567-6572 (2002).
Vrooman et al., "Molecular markers for detection, surveillance and prognostication of bladder cancer," *Intern. Journ. of Urology*, vol. 16, No. 3, pp. (2009).
Epitomics: YBOX1 Rabbit Monoclonal Antibody Product Data Sheet, Apr. 1, 2005, XP55031538, 1 page.
Epitomics: "YBOX1 DyLight 488 Rabbit Monoclonal Antibody Product Data Sheet," Aug. 30, 2010, XP55031469, 2 pages.
Epitomics: "YB-1 (C-term) Rabbit Monoclonal Antibody Product Data sheet," Jul. 1, 2008, XP55031564, 1 page.
Shiota et al., "Twist1 and Y-box-binding protein-1 promote malignant potential in bladder cancer cells," *BJU International*, vol. 108, No. 2b, pp. E142-E149 (2010).

(Continued)

*Primary Examiner* — Andrea S Grossman
(74) *Attorney, Agent, or Firm* — Foley & Lardner LLP

(57) ABSTRACT

The present invention pertains to the field of cancer prediction. Specifically, it relates to a method for predicting the risk of recurrence of bladder cancer in a subject after treatment of bladder cancer comprising the steps of determining the amount of at least one biomarker selected from the biomarkers shown in Table, and comparing the amount of said at least one biomarker with a reference amount for said at least one biomarker, whereby the risk of recurrence of bladder cancer is to be predicted. The present invention also contemplates a method for identifying a subject being in need of a further bladder cancer therapy. Encompassed are, furthermore, diagnostic devices and kits for carrying out said methods.

9 Claims, 1 Drawing Sheet

(56) References Cited

OTHER PUBLICATIONS

Santa Cruz Biotechnology, Inc., Lamin A/C (N-18): sc-6215; Jun. 7, 2011, 2 pages.
USCN Life Science Inc., "Enzyme-linked Immunosorbent Assay Kit for Lamin A/C (LMNA)"; Jun. 2, 2011, 7 pages.
Barboro et al., "Differential proteomic analysis of nuclear matrix in muscle-invasive bladder cancer: Potential to improve diagnosis and prognosis"; *Cellular Oncology*, vol. 30, pp. 13-26 (2008).
Schröder et al., "Robust Protein Profiling with Complex Antibody Microarrays in a Dual-Colour Mode," *Methods Mol. Biol.*, vol. 785, pp. 203-221 (2011).
Alhamdani et al., "Analysis conditions for proteomic profiling of mammalian tissue and cell extracts with antibody microarrays," *Proteomics*, vol. 10, pp. 3203-3207 (2010).
Schroder et al., "Dual-color Proteomic Profiling of Complex Samples with a Microarray of 810 Cancer-related Antibodies," *Mol. Cell. Proteomics*, vol. 9, No. 6, pp. 1271-1280 (2010).
Alhamdani et al., "Single-Step Procedure for the Isolation of Proteins at Near-Native Conditions from Mammalian Tissue for Proteomic Analysis on Antibody Microarrays," *J. Proteomic Res.*, vol. 9, No. 2, pp. 963-971 (2010).
Alhamdani et al., "Oncoproteomic Profiling with Antibody Microarrays," *Genome Med.*, vol. 1, No. 7, pp. 68.1-68.7 (2009).
Kusnezow et al., "Antibody microarray-based profiling of complex speciments: systematic evaluation of labeling strategies," *Proteomics*, vol. 7, No. 11, pp. 1786-1799 (2007).
International Search Report issued in related International Patent Application No. PCT/EP2012/060876, completed Aug. 24, 2012.

\* cited by examiner

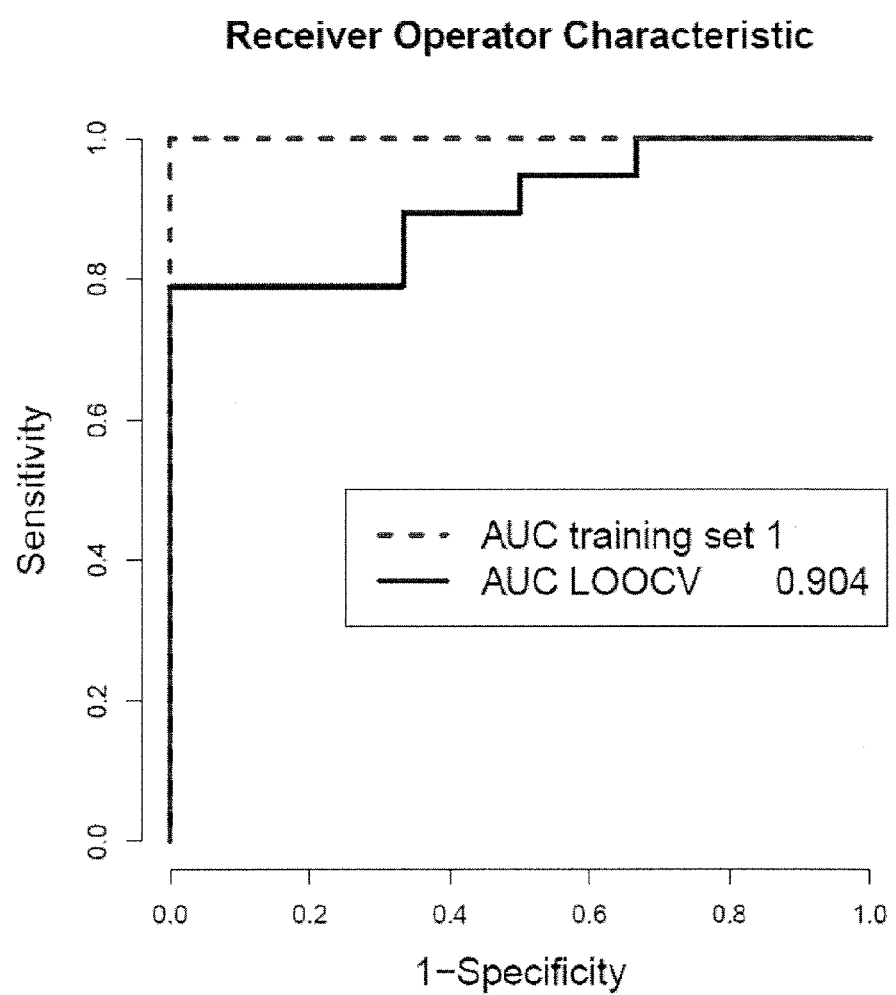

PREDICTION OF RECURRENCE FOR BLADDER CANCER BY A PROTEIN SIGNATURE IN TISSUE SAMPLES

The present invention pertains to the field of cancer prediction. Specifically, it relates to a method for predicting the risk of recurrence of bladder cancer in a subject after treatment of bladder cancer comprising the steps of determining the amount of at least one biomarker selected from the biomarkers shown in Table 1-3, and comparing the amount of said at least one biomarker with a reference amount for said at least one biomarker, whereby the risk of recurrence of bladder cancer is to be predicted. The present invention also contemplates a method for identifying a subject being in need of further bladder cancer therapy, a method for predicting the risk of progression of bladder cancer, a method for monitoring treatment of bladder cancer as well as method for monitoring progression of bladder cancer. Encompassed are, furthermore, diagnostic devices and kits for carrying out said methods.

Bladder cancer is the fourth most common type of cancer in men and the ninth most common cancer in women. Nonmuscle-invasive bladder cancer has a high propensity for recurrence. Since it usually requires life-long surveillance, it is one of the most expensive cancers to treat.

Proteins, as the end product or the acting products of gene expression play a vital role in all activities of a cell. Proteins, as readily available through many body fluids such as urine, plasma and tissue extracts provide the immediate option for clinical analysis. Proteomic technologies are important for the discovery of clinically relevant biomarkers in various types of cancers.

So far, only a few biomarkers have been described for assessing recurrence of bladder cancer. Karam et al. (Lancet Oncol. (2007); 8: 128-36) discloses that the apoptosis markers Bcl-2, P53, caspase-3, and P53 can be combined for prediction of bladder cancer recurrence and mortality after radical cystectomy. However, the wide spread application of such biomarkers depends on the accuracy of the detection methods for the individual mutations which are rather inconvenient at present. Thus, there is still a strong need for more reliable biomarkers for predicting the risk of recurrence and progression of bladder cancer. Moreover, diagnosis and further personalized treatment of subjects with bladder cancer, in particular nonmuscle-invasive bladder cancer, should be promoted.

Therefore, the present invention relates to a method for predicting the risk of recurrence of bladder cancer in a subject, comprising the steps of:
a) determining the amount of at least one biomarker selected from the biomarkers shown in Table 1 in sample from said subject, and
b) comparing the amount of said at least one biomarker with a reference amount for said at least one biomarker, whereby the risk of recurrence of bladder cancer is to be predicted.

The method as referred to in accordance with the present invention includes a method which essentially consists of the aforementioned steps or a method which includes further steps. However, it is to be understood that the method, in a preferred embodiment, is a method carried out ex vivo, i.e. not practised on the human or animal body. The method, preferably, can be assisted by automation.

The term "bladder cancer" as used herein refers to cancer of the bladder. In particular, the term refers to urothelial cell carcinoma (also known as "transitional cell carcinoma") which account for 90 percent of bladder cancers in industrial countries. The symptoms and implications accompanying bladder cancer are well known from standard text books of medicine such as Stedmen or Pschyrembl, like blood in the urine, pain during urination, frequent urination or feeling the need to urinate without being able to do so. In particular, the "bladder cancer" refers to disease in which the cells lining the urinary bladder lose the ability to regulate their growth resulting in a mass of cells that form a tumor. Preferably, the term encompasses numerous types of malignant growths of the urinary bladder. It is well known that Bladder cancer carries a broad spectrum of aggressiveness and risk. Usually, bladder cancer originates in the urothelium, a 3- to 7-cell mucosal layer within the muscular bladder. Preferably, bladder cancer as used herein refers to invasive bladder cancer. More preferable, the term refers to nonmuscle-invasive bladder cancer. Invasive bladder cancer has at least penetrated the muscular layer of the bladder wall, whereas nonmuscle-invasive bladder cancer is limited to the innermost linings of the bladder (known as the mucosa and lamina propria).

The most common staging system for bladder tumors is the TNM system. This staging system takes into account how deep the tumor has grown into the bladder, whether there is cancer in the lymph nodes and whether the cancer has spread to any other part of the body. According to the TNM (tumor, lymph node, and metastasis) staging system which is a pathologic staging system, bladder cancer can be also staged as follows: In bladder cancer stage 0, cancer cells are confined to the mucosa. In bladder cancer stage I the tumour invades the subepithelial connective tissue/lamina propria. In bladder cancer stage II cancer cells have invaded the muscularis propria but the tumour is still organ-confined. In bladder cancer stage III cancer cells have extended through the bladder wall to the perivesical tissue or to the Prostatic stroma, uterus or vagina. In bladder cancer stage IV cancer cells have proliferated to the lymph nodes, pelvic or abdominal wall, and/or other organs. The "bladder cancer" in the context of the present invention, may encompass any of the aforementioned stages. However, it is particular envisaged that the bladder cancer is stage 0 (in particular stage Ta and Tis) or stage 1 bladder cancer according to the aforementioned staging system. Accordingly, bladder cancer, as used herein, is a nonmuscle-invasive, in particular non-muscle-invasive low stage bladder cancer.

Moreover, bladder cancer can be graded according the 1973 World Health Organization classification. The bladder cancer to be assessed in the context of the method of the present invention, is preferably, low grade bladder cancer, in particular grade 1 or grade 2 according to this classification. Thus, the bladder cancer is preferably low grade, low stage bladder cancer.

For more information on grading on staging of bladder cancer see, Jacobs, Bruce L. (2010). Bladder Cancer in 2010. CA Cancer J Clin. 60(4):244-72, which herewith is incorporated by reference with respect to its entire disclosure content)

In accordance with the method of the present invention, the risk of recurrence of bladder cancer shall be predicted, and, thus, the risk of a subject to suffer from recurrent bladder cancer. Recurrent bladder cancer is a cancer that reappears in the urinary bladder (or in a nearby organ) after having being treated. Accordingly, the "recurrence of bladder cancer" as used herein refers to bladder cancer which recurs after treatment of bladder cancer. Preferably, it is predicted whether bladder cancer recurs within 1 year, 2 years, 3 years, 5 years, 10 years, 15 years, or 20 years, or any intermitting time range after said treatment. Preferably, it is predicted whether bladder cancer recurs within 2 years, or, more preferably, within 4 years after said treatment. The cancer recurrence may be a local recurrence or a distal recurrence. Local recurrence refers to cancers that recur in tissues or organs adjacent to or proximate to the urinary bladder, whereas distal recurrence refers to cancers that recur distant from the cancerous tissue or organ. Preferably, the cancer recurrence is a local recurrence. Recurrence and progression of bladder cancer is described, e.g., by Mansoor et al. in 2011 (J Coll Physicians Surg Pak. 21(3):157-160).

The term "predicting the risk" as used herein, preferably, refers to assessing the probability according to which bladder cancer bladder cancer will recur in a subject. More preferably, the risk/probability of recurrence of bladder cancer within a certain time window is predicted. In a preferred embodiment of the present invention, the predictive window, preferably, is an interval at least 1 month, at least 3 month, at least 6 month, at least 9 month, at least 1 year, at least 2 years, at least 3 years, at least 4 years, at least 5 years, at least 10 years, at least 15 years, or at least 20 years, or any intermitting time range. In a particular preferred embodiment of the present invention, the predictive window, preferably, is an interval of 2 years, or more preferably, of 4 years. In another preferred embodiment of the present invention, the predictive window will be the entire life span of the subject. Preferably, said the predictive window is calculated from the completion of treatment of bladder surgery. More preferably, said predictive window is calculated from the time point at which the sample to be tested has been obtained.

As will be understood by those skilled in the art, such a prediction is usually not intended to be correct for 100% of the subjects. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001. Preferably, the probability envisaged by the present invention allows that the prediction of an increased, normal or decreased risk will be correct for at least 60%, at least 70%, at least 80%, or at least 90% of the subjects of a given cohort or population. The term, preferably, relates to predicting whether a subject is at elevated risk or reduced risk as compared to the average risk for the recurrence of bladder cancer in a population of subjects.

The term "predicting the risk of recurrence of bladder cancer" as used herein means that the subject to be analyzed by the method of the present invention is allocated either into the group of subjects being at risk of recurrence of bladder cancer, or into the group of subjects being not at risk of recurrence of bladder cancer. A risk of recurrence of bladder cancer as referred to in accordance with the present invention, preferably, means that the risk of recurrence of bladder cancer is elevated (within the predictive window). Preferably, said risk is elevated as compared to the average risk in a cohort of subjects with bladder cancer (i.e. a group of subjects having been subjected to bladder cancer treatment). If a subject is not at risk of recurrence of bladder cancer as referred to in accordance with the present invention, preferably, the risk of recurrence of bladder cancer shall be reduced (within the predictive window). Preferably, said risk is reduced as compared to the average risk in a cohort of subjects with bladder cancer (i.e. a group of subjects having been subjected to bladder cancer treatment). A subject who is at risk of recurrence of bladder cancer preferably has a risk of 90% or larger, or, more preferably of 75% or larger of recurrence of bladder cancer, preferably, within a predictive window of 5 years. A subject who is at not at risk of recurrence of bladder cancer preferably has a risk of lower than 10%, more preferably of lower than, 10% or lower of recurrence of bladder cancer, preferably, within a predictive window of 5 years.

The term "subject" as used herein relates to animals, preferably mammals, and, more preferably, humans. The subject to be tested in the context of the method of the present invention shall suffer or shall have suffered from bladder cancer. Preferably, the method of the present invention shall be applied for subjects known to suffer from bladder cancer. More preferably, the method of the present invention is applied to a subject known to suffer from bladder cancer, wherein said subject i) will be treated against bladder cancer in the future, ii) is treated against bladder cancer or iii) has been treated against bladder cancer at the time at which the method is carried out (or to be more precise, at the time at which the sample is obtained). Preferred treatments of bladder cancer are disclosed elsewhere herein.

The term "biomarker" as used herein refers to a polypeptide as shown in Table 1 (and table 2 and 3, respectively) or a fragment or variant of such a polypeptide being associated to the recurrence of bladder cancer to the same extent as the polypeptides recited in Table 1 (and table 2 and 3, respectively). In the tables all biomarkers are uniquely described by the Uniprot identifier, the Uniprot accession ID, the respective gene code as defined by the human genome nomenclature consortium (HGNC) and the official protein name as provided by the Uniprot database. For more information on the protein, see the UniProt Database, in particular, the UniProt release 2011_06 of May 31, 2011, see also The UniProt Consortium Ongoing and future developments at the Universal Protein Resource Nucleic Acids Res. 39: D214-D219 (2011). Variants of said polypeptide as shown in the aforementioned tables include polypeptides which differ in their amino acid sequence due to the presence of conservative amino acid substitutions. Preferably, such variants have an amino acid sequence being at least 70%, at least 80%, at least 90%, at least 95%, at least 98%, or at least 99% identical over the entire sequence region to the amino acid sequences of the aforementioned specific polypeptides. Variants may be allelic variants, splice variants or any other species specific homologs, paralogs, or orthologs. Preferably, the percent identity can be determined by the algorithms of Needleman and Wunsch or Smith and Waterman. Programs and algorithms to carry out sequence alignments are well known by a skilled artisan. To carry out the sequence alignments, the program PileUp (J. Mol. Evolution, 25, 351-360, 1987, Higgins et al., CABIOS, 5 1989: 151-153) or the programs Gap and BestFit (Needleman 1970, J. Mol. Biol. 48; 443-453 and Smith 1981, Adv. Appl. Math. 2; 482-489), which are part of the GCG software packet (Genetics Computer Group, 575 Science Drive, Madison, Wis., USA 53711, Version 1991), are preferably to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

In the method according to the present invention, at least one biomarker of the afore-mentioned group of biomarkers, and thus of the human proteins as shown in Table 1, is to be determined. However, more preferably, a group of biomarkers will be determined in order to strengthen specificity and/or sensitivity of the assessment. Such a group, preferably, comprises at least 2, at least 3, at least 4, at least 5, at least 10 or up to all of the said biomarkers shown in the Tables. In addition to the specific biomarkers recited in the specification, other biomarkers may be, preferably, determined as well in the methods of the present invention. Preferred combinations of biomarkers are disclosed herein elsewhere.

In a preferred embodiment of the method of the invention, said at least one biomarker is selected from the group of biomarkers listed in Table 2. An increase in such a biomarker in a sample of a test subject as compared to the reference is indicative for the risk of recurrence of bladder cancer. Moreover, a decrease in such a biomarker as compared to the reference, preferably, indicates that the subject is not a risk of recurrence of bladder cancer.

In another preferred embodiment of the method of the invention, said at least one biomarker is selected from the group of biomarkers listed in Table 3. A decrease in such a biomarker as compared to the reference amount is indicative for the risk of recurrence of bladder cancer. Moreover, an increase in such a biomarker as compared to the reference, preferably, indicates that the subject is not a risk of recurrence of bladder cancer.

The term "treatment of bladder cancer" as used herein encompasses any treatment regimen that aims to treat bladder cancer. Such treatment regimens are well known in the art. Preferably, the treatment of bladder cancer is selected from surgery, radiation therapy, immunotherapy and chemotherapy. The most preferred treatment of bladder cancer is surgery in which the tumor is removed from the bladder. A particular preferred surgery is transurethral resection of the tumor. Transurethral resection is, preferably, carried out for low grade, low stage cancers. In this surgery, the tumor is shaved off the bladder wall with a heated wire and the area is treated with diathermy—a mild electric current that reduces bleeding. Said resection may be carried out with or without adjuvant intravesical therapy.

The term "intravesical therapy", as used herein, preferably, refers to the instillation of a biological agent or a chemotherapy drug directly into the bladder. Said instillation is done in order to destroy any residual cancer cells. Intravesical therapy is a form of local drug therapy whereby the treatment is targeted directly at the site of the cancer (bladder) as opposed to systemic drug therapy where a drug is injected into a vein or is given orally and travels throughout the circulatory system in order to reach the bladder.

The most preferred intravesical therapy is intravesical immunotherapy, in particular immunotherapy with *Bacillus* Calmette-Guerin (BCG). This therapy allows for boosting the body's natural immune system to destroy the bladder cancer cells.

Also preferred is intravesical chemotherapy in which a chemotherapeutic agent is administered. Preferred agents are mitomycin C and thiotepa. Further preferred agents are pirarubicin and epirubicin.

A further preferred surgery is cystectomy, in particular radical or partial cystectomy. The term "cystectomy" refers to removal of all (radical cystectomy) or part (partial cystectomy) removal of the urinary bladder. This kind of surgery is usually carried out in invasive, in particular muscle invasive, bladder cancer.

The term "sample" as used herein refers to a sample of a body fluid, to a sample of separated cells, or to a sample from a tissue or an organ. Samples of body fluids can be obtained by well known techniques and include, preferably, samples of urine or more preferably, samples of blood, plasma, serum. Tissue or organ samples may be obtained from any tissue, in particular from tumor tissue, of an organ, in particular from the bladder, by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the polypeptides referred to herein.

As set forth above, it is particular preferred that the sample is obtained from the bladder. Preferably, the sample is bladder carcinoma tissue (and, thus, tumor tissue). How to obtain such as sample is well known in the art (in particular the sample can be obtained by biopsy or resection). More preferably, said sample is bladder carcinoma tissue obtained during removal of said tissue by surgery.

The sample to be analyzed in the context of the methods of the present invention may be obtained prior, during or after treatment of bladder cancer, in particularly prior, during, or after the surgery as described herein. A sample obtained prior to treatment is, in an increasing order of preference, obtained not more than one year, not more than six, five, four, three or two months, or one month prior to the initiation of said treatment, in particular during the start of surgery. It is also contemplated to obtain a sample not more than two weeks, or not more than one week prior to said treatment. A sample obtained after treatment preferably, can be obtained after the end of the treatment, e.g. after completion of surgery. A sample obtained after treatment is, in an increasing order of preference not more than three years, obtained not more one year, not more than six, five, four, three or two months, or one month after said treatment. It is also contemplated to obtain a sample not more than two weeks, or not more than one week after said treatment. As set forth above, it is particularly envisaged that the sample has been obtained during the treatment, in particular during surgery.

Determining the amount of the polypeptide biomarkers referred to in this specification relates to measuring the amount or concentration, preferably semi-quantitatively or quantitatively. Measuring can be done directly or indirectly. Direct measuring relates to measuring the amount or concentration of the polypeptide based on a signal which is obtained from the polypeptide itself and the intensity of which directly correlates with the number of molecules of the polypeptide present in the sample. Such a signal—sometimes referred to herein as intensity signal may be obtained, e.g., by measuring an intensity value of a specific physical or chemical property of the polypeptide. Indirect measuring includes measuring of a signal obtained from a secondary component (i.e. a component not being the polypeptide itself) or a biological read out system, e.g., measurable cellular responses, ligands, labels, or enzymatic reaction products.

In accordance with the present invention, determining the amount of a polypeptide biomarker can be achieved by all known means for determining the amount of a polypeptide in a sample.

Said means comprise immunoassay devices and methods which may utilize labeled molecules in various sandwich, competition, or other assay formats. Preferably, the immunoassay device is an antibody array, in particular a planar antibody microarray, a bead based array (e.g. provided by Luminex Corporation, Austin, USA). Also preferred are stripe tests. Said assays will develop a signal which is indicative for the presence or absence of the polypeptide and, thus, the biomarker.

Moreover, the signal strength can, preferably, be correlated directly or indirectly (e.g. reverse-proportional) to the amount of polypeptide present in a sample. Further suitable methods comprise measuring a physical or chemical property specific for the polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays, CBA (an enzymatic Cobalt Binding Assay), and latex agglutination assays.

Preferably, determining the amount of a polypeptide biomarker comprises the steps of (a) contacting a cell capable of eliciting a cellular response the intensity of which is indicative of the amount of the polypeptide with the said polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the polypeptide.

Also preferably, determining the amount of a polypeptide biomarker comprises the step of measuring a specific intensity signal obtainable from the polypeptide in the sample. As described above, such a signal may be the signal intensity observed at a mass to charge (m/z) variable specific for the polypeptide observed in mass spectra or a NMR spectrum specific for the polypeptide.

Determining the amount of a polypeptide biomarker may, preferably, comprise the steps of (a) contacting the polypeptide with a specific ligand, (b) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the polypeptide described herein. Preferred ligands include antibodies, nucleic acids, peptides or polypeptides such as receptors or binding partners for the polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab, scFv and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. Alternatively, chimeric mouse antibodies with rabbit Fc can be used. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the polypeptide. Specific binding according to the present invention means that the ligand or agent should not bind substantially to ("cross-react" with) another peptide, polypeptide or substance present in the sample to be analyzed. Preferably, the specifically bound polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following. First, binding of a ligand may be measured directly, e.g. by mass spectroscopy, NMR or surface plasmon resonance. Second, if the ligand also serves as a substrate of an enzymatic activity of the polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/polypeptide" complex or the ligand which was bound by the polypeptide, respectively, may be contacted with a suitable substrate allowing detection by the generation of an intensity signal. For measurement of enzymatic reaction products, preferably the amount of substrate is saturating. The substrate may also be labeled with a detectable table prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of a tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemo luminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, or Dy-547, Dy-549, Dy-647, Dy-649 (Dyomics, Jena, Germany) or Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}S$, $^{125}I$, $^{32}P$, $^{33}P$ and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), FRET based proximity assays (Anal Chem. 2005 Apr. 15; 77(8): 2637-42.) or Ligation proximity assays (Nature Biotechnology 20, 473-477 (2002), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The amount of a polypeptide biomarker may be, also preferably, determined as follows: (a) contacting a solid support comprising a ligand for the polypeptide as specified above with a sample comprising the polypeptide and (b) measuring the amount of polypeptide which is bound to the support. The ligand, preferably, chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(0:9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known, see e.g., U.S. Pat. No. 5,744,305.

The term "amount" as used herein encompasses the absolute amount of a biomarker, the relative amount or concentration of the said biomarker as well as any value or parameter which correlates thereto or can be derived therefrom. Such values or parameters comprise intensity signal values from all specific physical or chemical properties obtained from the said biomarker by direct measurements, e.g., intensity values in mass spectra or NMR spectra or surface Plasmon resonance spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the biomarker comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount, while a concentration is compared to a reference concentration, or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount determined in step a) and the reference amount, it is possible to predict the risk of recurrence of bladder cancer in a subject after treatment of bladder cancer.

The term "reference" as used herein refers to amounts of the biomarker which allow for predicting whether a subject is at risk of recurrence of bladder cancer, or not. Therefore, the reference may either be derived from (i) a subject known to be at risk of recurrence of bladder cancer (or from a group of said subjects) or (ii) a subject known not to be at risk of recurrence of bladder cancer. Preferably, said reference is derived from a sample of the aforementioned subjects. More preferably, an increased amount of the said at least one biomarker selected from the biomarkers shown in Table 2 compared to the reference is indicative for a subject being at risk of recurrence of bladder cancer, whereas a decreased amount of the said at least one biomarker selected from the biomarkers shown in Table 2 compared to the reference is indicative for a subject not being at risk of recurrence of bladder cancer. Also preferably, an increased amount of the said at least one biomarker selected from the biomarkers shown in Table 3 compared to the reference is indicative for a subject not being at risk of recurrence of bladder cancer, whereas a decreased amount of the said at least one biomarker selected from the biomarkers shown in Table 3 compared to the reference is indicative for a subject being at risk of recurrence of bladder cancer.

Preferably, the increases or decreases as referred to herein are statistically significant. Whether an increase or decrease is statistically significant can be determined by the skilled person without further ado.

In the context of the methods of the present invention, the amount of more than one biomarker may be determined Of course, the, thus, determined amounts shall be compared to various reference amounts, i.e. to the reference amounts for the individual biomarker tested.

Moreover, the references, preferably, define threshold amounts or thresholds. Suitable reference amounts or threshold amounts may be determined by the method of the present invention from a reference sample to be analyzed together, i.e. simultaneously or subsequently, with the test sample. A preferred reference amount serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques. A suitable technique may be to determine the median of the population for the peptide or polypeptide amounts to be determined in the method of the present invention. Suitable threshold amounts can also be identified by ROC plots depicting the overlap between the two distributions by plotting the sensitivity versus 1–specificity for the complete range of decision thresholds. On the y-axis is sensitivity, or the true-positive fraction, defined as (number of true-positive test results)/(number of true-positive+number of false-negative test results). This has also been referred to as positivity in the presence of a given disease. It is calculated solely from the affected subgroup. On the x-axis is the false-positive fraction, or 1–specificity, defined as (number of false-positive results)/(number of true-negative+number of false-positive results). It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45 degrees diagonal line from the lower left corner to the upper right corner. Most plots fall in between these two extremes.

Further preferred are the following diagnostic algorithms:
i) An essentially identical or an increased amount of the at least one biomarker as compared to the reference amount indicates that the subject is at risk of recurrence of bladder cancer, if the at least one biomarker is selected from the biomarkers shown in Table 2, and if the reference amount is derived from a subject known to be at risk of recurrence of bladder cancer, and/or (ii) an essentially identical or a decreased amount of the at least one biomarker as compared to the reference amount indicates that the subject is at not risk of recurrence of bladder cancer, if the at least one biomarker is selected from the biomarkers shown in Table 2, and if the reference amount is derived from a subject known to be not at risk of recurrence of bladder cancer.
ii) An essentially identical or a decreased amount of the at least one biomarker as compared to the reference amount indicates that the subject is at risk of recurrence of bladder cancer, if the at least one biomarker is selected from the biomarkers shown in Table 3, and if the reference amount is derived from a subject known to be at risk of recurrence of bladder cancer, and/or an essentially identical or an increased amount of the at least one biomarker as compared to the reference amount indicates that the subject is not at risk of recurrence of bladder cancer, if the at least one biomarker is selected from the biomarkers shown in Table 3, and if the reference amount is derived from a subject known to be not at risk of recurrence of bladder cancer.

Advantageously, it has been found in the study underlying the present invention that the biomarkers listed in the Tables 1 are reliable markers for predicting the risk of recurrence of bladder cancer in a subject treated against bladder cancer. Said prediction is of high importance since bladder cancer, in particular nonmuscle-invasive bladder cancer, has a high degree of recurrence. Therefore, bladder cancer usually requires life-long monitoring, resulting in high health care costs. The findings underlying the aforementioned method also allow for an improved clinical management of bladder cancer since subjects can be identified which need intensive monitoring, or which do not need intensive monitoring. Furthermore, said findings of said method of the present invention also give hope to subjects being identified to be not of risk of recurrence of bladder cancer and, therefore, avoid misdirected and unnecessary treatment. Further, the success of a therapy can be monitored. In the studies underlying this invention, tissue samples from subjects after treatment of bladder cancer were analyzed using antibody microarrays comprising 810 antibodies against 741 different polypeptides. It was assessed whether there are differences between subjects in which bladder cancer recurred and subjects in which bladder cancer did not recur in the follow-up period. Differences in the polypeptide amounts between subjects which turned out to be statistically significant are shown in the Tables 1, 2 and 3 below and could be used as biomarkers for predicting the risk of recurrence of bladder cancer. Table 1 shows an overview of all biomarkers with modulated expression with respect to bladder cancer recurrence. Table 2 shows an overview on biomarkers which were increased in subjects in which bladder cancer recurred after treatment. Table 3 shows an overview on biomarkers which were decreased in subjects in which bladder cancer recurred after treatment. Thus, increased amounts of the biomarkers shown in table 2, and decreased amounts of the biomarkers shown in table 3 are associated with bladder cancer recurrence.

It is to be understood that a subject who is at risk of bladder cancer recurrence requires closer monitoring, and thus, shorter surveillance intervals as a subject who is not at risk of bladder cancer recurrence.

Therefore, the aforementioned method, preferably, further comprises the step of recommending the duration of surveillance intervals for the subject suffering from bladder cancer. Preferably, short surveillance intervals are recommended, if the subject is at risk of bladder cancer recurrence. Preferably, long surveillance intervals are recommended, if the subject is not at risk of bladder cancer recurrence. A short surveillance interval is, preferably, an interval of 5 months. More preferably, it is an interval of 4 months. Most preferably, it is an interval of 3 months or less. A long surveillance interval is, preferably, an interval of 9 months. More preferably, it is an interval of 1 year or more.

The definitions and explanations given herein above apply mutatis mutandis to the embodiments described herein below (except stated otherwise).

Moreover, the present invention relates to a method identifying a subject being in need of further bladder cancer therapy, comprising the steps of:
 a. determining the amount of at least one biomarker selected from the biomarkers shown in Table 1 in a sample from the subject, and
 b. comparing the amount of said at least one biomarker with a reference amount for said at least one biomarker, whereby a subject being in need of further bladder cancer therapy is to be identified.

The phrase "a subject in need of further bladder cancer therapy" as used herein relates to a subject who is at risk of recurrence of bladder cancer (as diagnosed by method described above). It will be understood that further bladder cancer therapy is at least beneficial for such subject. As discussed above, the diagnostic method of the present invention already allows identifying subjects being at risk of recurrence of bladder cancer shortly after treatment. Accordingly, such subjects which may not be unambiguously identifiable based on their clinical symptoms.

Preferred treatments of bladder cancer are described herein above. Preferred further bladder cancers therapies are, preferably, the described treatment regimens. More preferably, said further bladder cancer therapy is adjuvant intravesical therapy, preferably, immunotherapy or chemotherapy.

Preferably, the reference is derived from a subject or group of subjects known to be in need of further bladder cancer therapy, or from a subject or group of subjects known to be not in need of further bladder cancer therapy.

Preferably, the said at least one biomarker is selected from the group of biomarkers listed in Table 2, and wherein an increase in the said at least one biomarker as compared to the reference amount indicates that the subject is in need of further bladder cancer therapy, and/or wherein a decrease indicates that the subject is not in need of further bladder cancer therapy.

Preferably, the said at least one biomarker is selected from the group of biomarkers listed in Table 3, wherein a decrease in the said at least one biomarker as compared to the reference amount indicates that the subject is in need of further bladder cancer therapy and/or wherein an increase indicates that the subject is not in need of further bladder cancer therapy.

The term "sample" has been described herein above. Preferably, the sample to be tested has been obtained after treatment of bladder cancer. More preferably, the sample has been obtained during treatment of bladder cancer, in particular, during surgery.

Moreover, the present invention relates to a method for predicting the risk of progression of bladder cancer in a subject suffering from bladder cancer, comprising the steps of the aforementioned method of predicting the risk of recurrence of bladder cancer, and the further step of predicting progression of bladder cancer.

In particular, the present invention present invention relates to a method for predicting the risk of progression of bladder cancer in a subject suffering from bladder cancer, comprising the steps of a) determining the amount of at least one biomarker selected from the biomarkers shown in table 1, 2, 3 in a sample from said subject, and
 b) comparing the amount of said at least one biomarker with a reference amount for said at least one biomarker, whereby the risk of progression of bladder cancer is to be predicted.

The definitions for the terms "bladder cancer", "amount", "comparing", "subject", and "reference amount" given above apply accordingly. However, in the context of the aforementioned method is also contemplated that the subject suffering from bladder cancer may be also untreated (with respect to bladder cancer). Therefore, the sample to be used in the context of the aforementioned method may be obtained at any time-point after the onset of bladder cancer. In a more preferred embodiment, however, the sample is obtained as set forth in connection with the method for predicting the risk of recurrence of bladder cancer in a subject, in particular in low grade, low stage bladder cancer.

Preferably, the at least one biomarker is selected from table 2. More preferably, an increased amount of the said at least one biomarker selected from the biomarkers shown in Table 2 compared to the reference is indicative for a subject being at risk of progression of bladder cancers, whereas a decreased amount of the said at least one biomarker selected from the biomarkers shown in Table 2 compared to the reference is indicative for a subject not being at risk of progression of bladder cancer.

Also preferably, the at least one biomarker is selected from table 3. More preferably, a decreased amount of the said at least one biomarker selected from the biomarkers shown in Table 3 compared to the reference is indicative for a subject being at risk of progression of bladder cancers, whereas an increased amount of the said at least one biomarker selected from the biomarkers shown in Table 3 compared to the reference is indicative for a subject not being at risk of progression. Preferably, the increases or decreases as referred to herein are statistically significant. Whether an increase or decrease is statistically significant can be determined by the skilled person without further ado.

It is to be understood that a subject who is at risk of progression of bladder cancer, preferably, shall be at increased risk of progression of bladder cancer, whereas a subject who is not at risk of progression of bladder cancer, preferably, is at decreased risk of progression of bladder cancer.

Preferred references may be obtained from a subject or group thereof known to be at risk of progression of bladder cancer, or from a subject or group of subjects known to be not at risk of recurrence of bladder cancer.

Moreover, the present invention relates to a method for monitoring progression of bladder cancer in a subject suffering from bladder cancer, comprising the steps of
 a) determining the amount of at least one biomarker selected from the biomarkers shown in table 1, 2 or 3 in a sample from said subject,
 b) determining the amount of said at least one biomarker in a second sample from said subject, said second sample being obtained after said first sample, and
 c) comparing the amount of said at least one biomarker in said first sample to the amount of said at least one biomarker in said second sample.

The term "monitoring progression of bladder cancer" as referred to above relates to keeping track of the status of the disease, i.e. of bladder cancer. Monitoring includes comparing the status of the disease as reflected by the amount of the biomarker in a first sample taken at a first time point to the status of the disease reflected by the amount of the biomarker in a second sample taken at a second time point.

Preferably, if an amount of at least one biomarker as shown in table 2 is determined, the following applies: The status of the disease became worse and, thus, there was progression of the disease, if the amount of the biomarker is increased in the second sample as compared to the first sample, whereas there was amelioration and, thus, improvement of the status of the disease if the biomarker is decreased in the second sample as compared to the first sample. If no change is observed, i.e. an essentially identical amount is determined in the first and the second sample, the status of the disease remained unchanged and the disease, thus, was stagnating. An essentially identical amount is determined if no statistically significant change in the amount is determined between the first and the second sample. Whether the amounts are essentially identical can be determined by the skilled artisan without further ado.

Preferably, if the amount of the marker of the at least one biomarker as shown in table 3 was determined, the following applies: The status of the disease became worse and, thus, there was progression of the disease, if the amount of the biomarker is decreased in the second sample as compared to the first sample, whereas there was amelioration and, thus, improvement of the status of the disease if the biomarker is increased in the second sample as compared to the first sample. If no change is observed, i.e. an essentially identical amount is determined in the first and the second sample, the status of the disease remained unchanged and the disease, thus, was stagnating.

Accordingly, the following diagnostic algorithms are particularly preferred:

Preferably, an increase of the amount of at least one biomarker as shown in Table 2 in the second sample as compared to the first sample is indicative for the diagnosis of progression of bladder cancer. Preferably, a decrease of the amount of at least one biomarker as shown in Table 2 in the second sample as compared to the first sample is indicative for the diagnosis of amelioration of bladder cancer. Preferably, an essentially identical amount in the first and second sample is indicative for stagnation of bladder cancer.

Preferably, a decrease of the amount of at least one biomarker as shown in Table 3 in the second sample as compared to the first sample is indicative for the diagnosis of progression of bladder cancer. Preferably, an increase of the amount of at least one biomarker as shown in Table 3 in the second sample as compared to the first sample is indicative for the diagnosis of amelioration of bladder cancer. Preferably, an essentially identical amount in the first and second sample is indicative for stagnation of bladder cancer.

Preferably, a change, i.e. increase or decrease is significant if the amounts differ by at least about 5%, at least about 10%, at least about 15%, at least about 20%, at least about 25% or at least about 50%.

The term "sample" has been described elsewhere herein. The "first sample", in principle, can be obtained at any time point after the onset or diagnosis of bladder cancer. Preferably, however, it is obtained as in cancers being in stage 0 or 1 according to the TMN staging system and/or being graded as grade 1 or 2 according to the WHO classification system (see above). Also, preferably, it may be obtained during surgery (for preferred surgeries, see elsewhere herein). The "second sample" is, preferably, understood as a sample which is obtained in order to reflect a change of the amount of the at least biomarker as compared to the amount of the respective marker in the first sample. Thus, second sample shall be obtained after the first sample. Preferably, the second sample is not obtained too early after the first sample (in order to observe a sufficiently significant change to allow for monitoring). In accordance with the method of the present invention, the second sample is preferably obtained within a period of 1 month to 2 years after the first sample. Preferably, said second sample is obtained two years, or one year after the first sample. More preferably, said second sample is obtained 9 months after the first sample. Even more preferably, said second sample is obtained 6 months after the first sample. Most preferably, said second sample is obtained 3 months after the first sample.

Further envisaged by the present invention is a method for monitoring treatment of bladder cancer in a subject suffering from bladder cancer, comprising the steps of
 a) determining the amount of at least one biomarker selected from the biomarkers shown in tables 1 to 3 in a from sample from said subject,
 b) determining the amount of said at least one biomarker in a second sample from said subject, said second sample being obtained after said first sample, and
 c) comparing the amount of said at least one biomarker in said first sample to the amount of said at least one biomarker in said second sample, whereby treatment of cancer is monitored.

The term "monitoring treatment of bladder cancer" as used herein, preferably, relates to assessing the effects of treatment of bladder cancer, i.e. to assess whether treatment of bladder cancer is successful or not. Preferably, a treatment is considered as successful, if the condition of the subject with respect to bladder cancer did ameliorate. Preferably, a treatment is considered as not successful, if the condition of the subject with respect to bladder cancer worsened progress. Preferred methods of treatments of bladder cancer are described elsewhere herein. Preferably, the treatment is surgery and/or adjuvant intravesical therapy (see explanations elsewhere).

The following diagnostic algorithms are particularly preferred:

Preferably, the at least one biomarker is selected from the group of biomarkers shown in Table 2. Preferably, a decrease of the amount of at least one biomarker as shown in Table 2 in the second sample as compared to the first sample is indicates that the treatment is successful. Preferably, an increase of the amount of at least one biomarker as shown in Table 2 in the second sample as compared to the first sample indicates that the treatment is not successful.

Preferably, the at least one biomarker is selected from the group of biomarkers shown in Table 3. Preferably, an increase of the amount of at least one biomarker as shown in Table 3 in the second sample as compared to the first sample indicates that the treatment is successful. Preferably, a decrease of the amount of at least one biomarker as shown in Table 3 in the second sample as compared to the first sample indicates that the treatment is not successful.

Preferably, a change, i.e. increase or decrease is statistically significant if the amounts differ by at least 5%, at least 10%, at least 15%, at least 20%, at least 25% or at least 50% (see also above).

Preferred samples have been described elsewhere herein. The "first sample", in principle, can be obtained before or during treatment of bladder cancer. If the treatment is surgery, the first sample is preferably obtained during surgery. The "second sample" is, preferably, understood as a sample which is obtained in order to reflect a change of the amount of the at least biomarker as compared to the amount of the respective marker in the first sample. Thus, second sample shall be obtained after the first sample. In principle, the second sample is obtained during or after treatment of bladder cancer. Preferably, the second sample is not obtained too early after the first sample (in order to observe a sufficiently significant change to allow for monitoring). Thus, said second sample is, preferably, obtained one year after the first sample. More preferably, said second sample is obtained 9 months after the first sample. Even more preferably, said second sample is obtained 6 months after the first sample. Most preferably, said second sample is obtained 3 months after the first sample. If the treatment is surgery, it is particularly contemplated that the first sample is obtained before or during surgery and that the second sample is obtained after surgery.

Moreover, the present invention relates to the use of at least one biomarker selected from the group of biomarkers shown in Table 1, 2 or 3, or of a detection agent for said at least one biomarker for predicting the risk of recurrence of bladder cancer in a subject after treatment of bladder cancer, for identifying a subject being in need of further bladder cancer therapy, for predicting the risk of progression of bladder cancer, for monitoring progression of bladder cancer, or for monitoring treatment of bladder cancer.

The term "detection agent" as used herein refers to an agent which is capable of specifically recognizing and binding a biomarker selected from the biomarkers shown in table 1. The agent shall allow for direct or indirect detection of the complex formed by the said agent and the biomarker. Direct detection can be achieved by including into the agent a detectable label. Indirect labelling may be achieved by a further agent which specifically binds to the complex comprising the biomarker and the detection agent wherein the said further agent is than capable of generating a detectable signal. Suitable compounds which can be used as detection agents are well known in the art. Preferably, the detection agent is an antibody or aptamere which specifically binds to the biomarker protein or a nucleic acid encoding the biomarker. The term "antibody" as used herein includes both polyclonal and monoclonal antibodies, as well as any modifications or fragments thereof, such as Fv, Fab and F(ab) 2 fragments. The antibody shall be capable of specifically binding a biomarker selected from the biomarkers shown in table 1.

In an embodiment of the method of the present invention, the amount of at least one biomarker selected from the group consisting of FAS, IL-1B, IL-8, DEFB4, CTSS and IL-17B is determined in step a) instead of the at least one biomarker shown in Table 1.

The present invention also relates to a device for predicting recurrence of bladder cancer or for the prediction of progression of bladder cancer in a sample of a subject comprising:
a. an analyzing unit for the said sample of the subject comprising a detection agent for at least one biomarker as shown in Table 1, Table 2 or Table 3, said detection agent allowing for the determination of the amount of the said at least one biomarker in the sample; and operatively linked thereto, and
b. an evaluation unit comprising a data processing unit and a data base, said data base comprising a stored reference and said data processing unit being capable of carrying out a comparison of the amount of the at least one biomarker determined by the analyzing unit and the stored reference thereby establishing the prediction.

Preferred references are disclosed herein elsewhere.

The term "device" as used herein relates to a system of means comprising at least the afore-mentioned analyzing unit and the evaluation unit operatively linked to each other as to allow the diagnosis. Preferred detection agents to be used for the device of the present invention are disclosed above in connection with the method of the invention. Preferably, detection agents are antibodies or aptameres. How to link the units of the device in an operating manner will depend on the type of units included into the device. For example, where units for automatically determining the amount of the biomarker are applied, the data obtained by said automatically operating unit can be processed by, e.g., a computer program in order to obtain the desired results. Preferably, the units are comprised by a single device in such a case. The computer unit, preferably, comprises a database including the stored reference(s) as well as a computer-implemented algorithm for carrying out a comparison of the determined amounts for the polypeptide biomarkers with the stored reference of the database. Computer-implemented as used herein refers to a computer-readable program code tangibly included into the computer unit. The results may be given as output of raw data which need interpretation by the clinician. Preferably, the output of the device is, however, processed, i.e. evaluated, raw data the interpretation of which does not require a clinician.

In a preferred device of the invention, the detection agent, preferably, an antibody, is immobilized on a solid support in an array format. It will be understood that a device according to the present invention can determine the amount of more than one biomarker simultaneously. To this end, the detection agents may be immobilized on a solid support and arranged in an array format, e.g., in a so called "microarray".

The present invention also relates to a kit comprising a detection agent for determining the amount of at least one biomarker as shown in any one of Tables 1 to 3 and evaluation instructions for establishing the diagnosis.

The term "kit" as used herein refers to a collection of the aforementioned agent and the instructions provided in a ready-to-use manner for determining the biomarker amount in a sample. The agent and the instructions are, preferably, provided in a single container. Preferably, the kit also comprises further components which are necessary for carrying out the determination of the amount of the biomarker. Such components may be auxiliary agents which are required for the detection of the biomarker or calibration standards. Moreover, the kit may, preferably, comprise agents for the detection of more than one biomarker.

In the context of the present invention, it is particularly envisaged to determine the amount of more than one biomarker, e.g., for predicting the risk of recurrence of bladder cancer. The combined determination of biomarkers of is advantageous since it allows for a higher specificity and sensitivity, e.g., when predicting the risk of recurrence of bladder cancer.

The following combinations of biomarkers are particularly preferred in accordance with the methods, kits, devices, and uses of the present invention:
a combination of LMNA, YBOX1, and JUN
a combination of LMNA, YBOX1, JUN, AKT3, and SMAD3
a combination of LMNA, YBOX1, JUN, AKT3, SMAD3, LYAM1, and PABP1.
a combination of LMNA, YBOX1, JUN, AKT3, SMAD3, LYAM1, PABP1, TIA1, CASP3, CDN1A, CASP9, and YETS2 a combination of LMNA, YBOX1, JUN, AKT3, SMAD3, LYAM1, PABP1, TIA1, CASP3, CDN1A, CASP9, YETS2, PO2F2, TOP2A, and RSSA.

a combination of LMNA, YBOX1, JUN, AKT3, SMAD3, LYAM1, PABP1, TIA1, CASP3, CDN1A, CASP9, YETS2, PO2F2, TOP2A, RSSA, NFAC4, ZBT17, AKTIP, HSP7C, and LIFR.

Whether the increased or decreased amounts of the various biomarkers are indicative for a condition or risk as referred to herein can be derived from Tables 2 and 3.

A combination of the aforementioned markers will increase sensitivity and specificity of the diagnostic assay.

Further, it is envisaged to determine a combination of at least three biomarkers as set forth in Table 1 in accordance with the present invention. In particular, is it envisaged to determine a combination of at least three biomarkers selected from the aforementioned biomarkers, i.e. from LMNA, YBOX1, JUN, AKT3, SMAD3, LYAM1, PABP1, TIA1, CASP3, CDN1A, CASP9, YETS2, PO2F2, TOP2A, RSSA, NFAC4, ZBT17, AKTIP, HSP7C, and LIFR. The phrase "at least three", preferably, means three or more than three. In particular, it is envisaged to determine at least 5, at least 8, at least 10, or at least 15 biomarkers.

The present invention also envisages a composition, or a kit comprising a detection agent which specifically binds to LMNA, a detection agent which specifically binds to YBOX1, and a detection agent which specifically binds to JUN. For a further explanation of these biomarkers, see tables 1 to 3.

The present invention also envisages a composition, or a kit comprising a detection agent which specifically binds to LMNA a detection agent which specifically binds to YBOX1, a detection agent which specifically binds to JUN, a detection agent which specifically binds to AKT3, and a detection agent which specifically binds to SMAD3.

The present invention also envisages a composition, or a kit, said composition or kit comprising a detection agent which specifically binds to LMNA, a detection agent which specifically binds to YBOX1, a detection agent which specifically binds to JUN, a detection agent which specifically binds to AKT3, a detection agent which specifically binds to SMAD3, a detection agent which specifically binds to LYAM1, and a detection agent which specifically binds to PABP1.

The present invention also envisages a composition, or a kit, said composition or kit comprising a detection agent which specifically binds to LMNA, a detection agent which specifically binds to YBOX1, a detection agent which specifically binds to JUN, a detection agent which specifically binds to AKT3, a detection agent which specifically binds to SMAD3, a detection agent which specifically binds to LYAM1, a detection agent which specifically binds to PABP1, a detection agent which specifically binds to TIA1, a detection agent which specifically binds to CASP3, and a detection agent which specifically binds to CDN1A, and a detection agent which specifically binds to CASP9, a detection agent which specifically binds to YETS2.

The present invention also envisages a composition, or a kit, said composition or kit comprising a detection agent which specifically binds to LMNA, a detection agent which specifically binds to YBOX1, a detection agent which specifically binds to JUN, a detection agent which specifically binds to AKT3, a detection agent which specifically binds to SMAD3, a detection agent which specifically binds to LYAM1, a detection agent which specifically binds to PABP1, a detection agent which specifically binds to TIA1, a detection agent which specifically binds to CASP3, a detection agent which specifically binds to CDN1A, a detection agent which specifically binds to CASP9, a detection agent which specifically binds to YETS2, a detection agent which specifically binds to PO2F2, and a detection agent which specifically binds to TOP2A, a detection agent which specifically binds to RSSA.

The present invention also envisages a composition, or a kit, said composition or kit comprising a detection agent which specifically binds to LMNA, a detection agent which specifically binds to YBOX1, a detection agent which specifically binds to JUN, a detection agent which specifically binds to AKT3, a detection agent which specifically binds to SMAD3, a detection agent which specifically binds to LYAM1, a detection agent which specifically binds to PABP1, a detection agent which specifically binds to TIA1, a detection agent which specifically binds to CASP3, a detection agent which specifically binds to CDN1A, a detection agent which specifically binds to CASP9, a detection agent which specifically binds to YETS2, a detection agent which specifically binds to PO2F2, a detection agent which specifically binds to TOP2A, a detection agent which specifically binds to RSSA, a detection agent which specifically binds to NFAC4, a detection agent which specifically binds to ZBT17, a detection agent which specifically binds to AKTIP, and a detection agent which specifically binds to HSP7C, and a detection agent which specifically binds to LIFR.

It is particularly envisaged that the detection agents, preferably, an antibody or fragment thereof, comprised by the aforementioned kits or compositions are immobilized on a solid support in an array format. In particular, the detection agents may be immobilized on a solid support and arranged in an array format, e.g., in a so called "microarray". Accordingly, the present invention also envisaged a microarray comprising the aforementioned detection agents.

Preferably, the kit, the composition and the microarray is used for predicting the risk of recurrence of bladder cancer in a sample of a subject.

All references cited in this specification are herewith incorporated by reference with respect to their entire disclosure content and the disclosure content specifically mentioned in this specification.

FIGURE LEGENDS

FIG. 1: With an random-forrest classifier applied to the training set, all samples were classified correctly (dashed line) corresponding to an area under the curve (AUC) of 100%. A cross validation with the Leave-One-Out method resulted in a good discrimination of the samples with an AUC of 90.4% (see also Examples).

The following Examples shall merely illustrate the invention. They shall not be construed, whatsoever, to limit the scope of the invention.

EXAMPLE 1

Identification of Polypeptide Biomarker to Predict the Risk of Recurrence of Bladder Cancer In order to identify polypeptides with differential abundance in bladder cancer patients with recurrent tumours compared to non-recurrent tumours a study was performed utilising complex antibody microarrays. In this study the protein fraction of the samples was directly labeled by a fluorescent dye, using NHS-ester chemistry. A reference was established by pooling all samples comprised in the study and labeled with a second fluorescent dye. For incubation each sample was mixed with the reference sample and incubated on an antibody microarray in a competitive dual-colour approach.

For inclusion on the array specific target proteins were selected based on the up- or downregulation in transcriptional studies for different cancer entities. The antibody microarray applied in this study comprised 810 antibodies that were directed at 741 different proteins. All antibodies were immobilised at least in duplicates. In addition, all incubations were performed in duplicates. The study involved samples from 19 patients with recurrent and six patients with non-recurrent bladder cancers. The tumours were classified as stage 0 (Ta or Tis) and low grade.

After protein extraction from the tissue samples using T-PER reagent (Thermo Fisher), the protein samples were labeled with Dy-549 (Dyomics, Jena, Germany). Additionally, a common reference was prepared by pooling of samples and subsequent labeling with Dy-649 (Dyomics). All protein samples were labeled at a protein concentration of 1 mg/mL with 0.1 mg/mL of the NHS-esters of the fluorescent dyes in 100 mM sodium bicarbonate buffer (pH 9.0) on a shaker at 4° C. After 1 h, the reactions were stopped by addition of 10% glycin. Unreacted dye was removed 30 min later and the buffer changed to PBS using Zeba Desalt columns (Thermo Scientific). Subsequently, Complete Protease Inhibitor Cocktail tablets (Roche, Mannheim, Germany) were added as recommended by the manufacturer.

Homemade incubation chambers were attached to the array slides with Terostat-81 (Henkel, Dusseldorf, Germany). The inner dimensions of the incubation chambers matched the area of the array (9 mm×18 mm) with an additional border of 2 mm and a height of 5 mm. Prior to adding the labeled protein samples, the arrays were blocked with 10% skim milk powder and 0.05% Tween-20 in phosphate buffered saline (PBS) on a Slidebooster instrument (Advalytix, Munich, Germany) for 4 h. Incubation was performed with labeled samples diluted 1:60 in blocking solution containing 0.1% (w/v) Triton-X100 and Complete Protease Inhibitor Cocktail for 16 h in a total volume of 600 µL. Slides were thoroughly washed with PBSTT prior and after detaching the incubation chambers. Finally, the slides were rinsed with 0.1×PBS and distilled water and dried in a stream of air.

Slide scanning was done on a ScanArray 5000 or 4000 XL unit (Packard, Billerica, USA) using the identical instrument laser power and PMT in each experiment. Spot segmentation was performed with GenePix Pro 6.0 (Molecular Devices, Union City, USA). Resulting data were analyzed using the LIMMA package of R-Bioconductor after uploading the mean signal and median background intensities. For normalization an invariant Lowess normalization was applied (Sill M. et al. BMC Bioinformatics. 2010 11:556). For differential analyses of the depletion experiment a one-factorial linear model was fitted with LIMMA resulting in a two-sided t-test or F-test based on moderated statistics. All presented p-values were adjusted for multiple testing by controlling the false discovery rate according to Benjamini and Hochberg.

Using LIMMA analysis, 100 proteins were identified with differential abundance between recurrent and non-recurrent samples at a highly significant level of adj. $P<0.003$. The results of the aforementioned study are summarized in the following Tables. In the tables the difference of protein abundance in the two sample groups is given by the log fold change. The level of significance is indicated by the p-value adjusted for multiple testing as described above.

TABLE 1

Differentially regulated biomarkers (all)

| Nr | Uniprot Identifier | Log fold change | Adjusted p-value | Uniprot Accession | HGNC Symbol | Protein name |
|---|---|---|---|---|---|---|
| 1 | YBOX1_HUMAN | 0.52 | 1.87E−08 | P67809 | YBX1 | Nuclease-sensitive element-binding protein 1 |
| 2 | LMNA_HUMAN | 0.72 | 3.32E−09 | P02545 | LMNA | Lamin A, Prelamin-A/C, Lamin-A/C |
| 3 | JUN_HUMAN | 0.50 | 1.27E−07 | P05412 | JUN | Transcription factor AP-1 |
| 4 | PABP1_HUMAN | −0.36 | 2.13E−07 | P11940 | PABPC1 | Polyadenylate-binding protein 1 |
| 5 | SMAD3_HUMAN | −0.59 | 2.13E−07 | P84022 | SMAD3 | Mothers against decapentaplegic homolog 3 |
| 6 | TIA1_HUMAN | −0.39 | 2.13E−07 | P31483 | TIA1 | Nucleolysin TIA-1 isoform p40 |
| 7 | AKT3_HUMAN | 0.48 | 2.47E−07 | Q9Y243 | AKT3 | RAC-gamma serine/threonine-protein kinase |
| 8 | CDN1A_HUMAN | −0.52 | 3.38E−07 | P38936 | CDKN1A | Cyclin-dependent kinase inhibitor 1 |
| 9 | LYAM1_HUMAN | −0.52 | 9.62E−07 | P14151 | SELL | L-selectin |
| 10 | YETS2_HUMAN | 0.32 | 5.28E−06 | Q9ULM3 | YEATS2 | YEATS domain-containing protein 2 |
| 11 | AKTIP_HUMAN | −0.35 | 5.38E−06 | Q9H8T0 | AKTIP | AKT-interacting protein |
| 12 | HSP7C_HUMAN | −0.34 | 1.04E−05 | P11142 | HSPA8 | Heat shock cognate 71 kDa protein |
| 13 | PRI1_HUMAN | −0.36 | 1.04E−05 | P49642 | PRIM1 | DNA primase small subunit |
| 14 | RSSA_HUMAN | −0.35 | 1.07E−05 | P08865 | RSSA | 40S ribosomal protein SA |
| 15 | GRM1A_HUMAN | 0.27 | 1.10E−05 | Q96CP6 | GRAMD1A | GRAM domain-containing protein 1A |
| 16 | TPA_HUMAN | 0.23 | 1.14E−05 | P00750 | PLAT | Tissue-type plasminogen activator chain B |
| 17 | ZBT17_HUMAN | −0.55 | 1.14E−05 | Q13105 | ZBTB17 | Zinc finger and BTB domain-containing protein 17 |
| 18 | CADH1_HUMAN | 0.33 | 1.15E−05 | P12830 | CDH1 | E-Cad/CTF2 |
| 19 | LAMP2_HUMAN | 0.26 | 1.15E−05 | P13473 | LAMP2 | Lysosome-associated membrane glycoprotein 2 |
| 20 | LIFR_HUMAN | 0.30 | 2.17E−05 | P42702 | LIFR | Leukemia inhibitory factor receptor |
| 21 | TOP2A_HUMAN | 0.48 | 2.17E−05 | P11388 | TOP2A | DNA topoisomerase 2-alpha |
| 22 | SPS2L_HUMAN | −0.23 | 2.20E−05 | Q9NUQ6 | SPATS2L | SPATS2-like protein |
| 23 | NFAC4_HUMAN | 0.35 | 2.47E−05 | Q14934 | NFATC4 | Nuclear factor of activated T-cells, cytoplasmic 4 |
| 24 | SF3B3_HUMAN | 0.32 | 2.47E−05 | Q15393 | SF3B3 | Splicing factor 3B subunit 3 |
| 25 | UBIQ_HUMAN | 0.24 | 2.47E−05 | P62988 | UBC | Ubiquitin |
| 26 | 2DMB_HUMAN | −0.35 | 3.41E−05 | P28068 | HLA-DMB | HLA class II histocompatibility antigen, DM beta chain |
| 27 | FAK1_HUMAN | −0.36 | 3.93E−05 | Q05397 | PTK2 | Focal adhesion kinase 1 |
| 28 | IFNG_HUMAN | −0.46 | 3.95E−05 | P01579 | IFNG | Interferon gamma |
| 29 | SP1_HUMAN | −0.36 | 4.14E−05 | P08047 | SP1 | Transcription factor Sp1 |
| 30 | ACTN1_HUMAN | −0.36 | 4.31E−05 | P12814 | ACTN1 | Alpha-actinin-1 |
| 31 | TIE1_HUMAN | −0.30 | 6.17E−05 | P35590 | TIE1 | Tyrosine-protein kinase receptor Tie-1 |
| 32 | MMP13_HUMAN | 0.25 | 6.32E−05 | P45452 | MMP13 | Collagenase 3 |

TABLE 1-continued

Differentially regulated biomarkers (all)

| Nr | Uniprot Identifier | Log fold change | Adjusted p-value | Uniprot Accession | HGNC Symbol | Protein name |
|---|---|---|---|---|---|---|
| 33 | TIMP1_HUMAN | −0.33 | 6.32E−05 | P01033 | TIMP1 | Metalloproteinase inhibitor 1 |
| 34 | VTNC_HUMAN | −0.51 | 6.76E−05 | P04004 | VTN | Somatomedin-B |
| 35 | K1C17_HUMAN | −0.20 | 1.70E−04 | Q04695 | KRT17 | Keratin, type I cytoskeletal 17 |
| 36 | NFKB1_HUMAN | 0.32 | 1.76E−04 | P19838 | NFKB1 | Nuclear factor NF-kappa-B p105 subunit |
| 37 | NAP1_HUMAN | −0.27 | 1.91E−04 | Q9BU70 | C9orf156 | Nef-associated protein 1 |
| 38 | RL10_HUMAN | −0.28 | 1.91E−04 | P27635 | RPL10 | 60S ribosomal protein L10 |
| 39 | KLF5_HUMAN | 0.37 | 1.96E−04 | Q13887 | KLF5 | Krueppel-like factor 5 |
| 40 | MMP1_HUMAN | −0.26 | 2.27E−04 | P03956 | MMP1 | 27 kDa interstitial collagenase |
| 41 | CDKN3_HUMAN | −0.33 | 2.36E−04 | Q16667 | CDKN3 | Cyclin-dependent kinase inhibitor 3 |
| 42 | CD59_HUMAN | −0.33 | 2.56E−04 | P13987 | CD59 | CD59 glycoprotein |
| 43 | PO2F2_HUMAN | −0.35 | 2.56E−04 | P09086 | POU2F2 | POU domain, class 2, transcription factor 2 |
| 44 | MPIP2_HUMAN | −0.28 | 2.76E−04 | P30305 | CDC25B | M-phase inducer phosphatase 2 |
| 45 | FRAP_HUMAN | −0.27 | 2.78E−04 | P42345 | FRAP1 | Serine/threonine-protein kinase mTOR |
| 46 | IRS2_HUMAN | −0.33 | 3.10E−04 | Q9Y4H2 | IRS2 | Insulin receptor substrate 2 |
| 47 | B2LA1_HUMAN | 0.24 | 3.49E−04 | Q16548 | BCL2A1 | Bcl-2-related protein A1 |
| 48 | ERBB2_HUMAN | −0.24 | 3.65E−04 | P04626 | ERBB2 | Receptor tyrosine-protein kinase erbB-2 |
| 49 | CASP3_HUMAN | 0.40 | 3.99E−04 | P42574 | CASP3 | Caspase-3 subunit p17 |
| 50 | FINC_HUMAN | −0.31 | 3.99E−04 | P02751 | FN1 | Ugl-Y2 |
| 51 | LAC_HUMAN | −0.26 | 4.00E−04 | P01842 | IGLC3 | Ig lambda chain C regions |
| 52 | AURKB_HUMAN | −0.33 | 4.05E−04 | Q96GD4 | AURKB | Serine/threonine-protein kinase 12 |
| 53 | MPP3_HUMAN | −0.21 | 4.10E−04 | Q13368 | MPP3 | MAGUK p55 subfamily member 3 |
| 54 | CD2A2_HUMAN | −0.32 | 4.34E−04 | Q8N726 | CDKN2A | Cyclin-dependent kinase inhibitor 2A, isoform 4 |
| 55 | EPCAM_HUMAN | −0.30 | 4.39E−04 | P16422 | EPCAM | Epithelial cell adhesion molecule |
| 56 | SOX9_HUMAN | 0.23 | 4.39E−04 | P48436 | SOX9 | Transcription factor SOX-9 |
| 57 | TSP3_HUMAN | −0.24 | 4.39E−04 | P49746 | THBS3 | Thrombospondin-3 |
| 58 | MUC5B_HUMAN | 0.25 | 4.97E−04 | Q9HC84 | MUC5B | Mucin-5B |
| 59 | CP3A7_HUMAN | −0.23 | 5.54E−04 | P24462 | CYP3A7 | Cytochrome P450 3A7 |
| 60 | NMDE3_HUMAN | −0.27 | 5.62E−04 | Q14957 | GRIN2C | Glutamate [NMDA] receptor subunit epsilon-3 |
| 61 | THYG_HUMAN | −0.34 | 5.62E−04 | P01266 | TG | Thyroglobulin |
| 62 | AQP1_HUMAN | 0.24 | 6.21E−04 | P29972 | AQP1 | Aquaporin-1 |
| 63 | IL15_HUMAN | −0.80 | 6.21E−04 | P40933 | IL15 | Interleukin-15 |
| 64 | LAT1_HUMAN | −0.24 | 6.21E−04 | Q01650 | SLC7A5 | Large neutral amino acids transporter small subunit 1 |
| 65 | GSHB_HUMAN | 0.17 | 6.35E−04 | P48637 | GSS | Glutathione synthetase |
| 66 | RPB3_HUMAN | −0.23 | 6.58E−04 | P19387 | POLR2C | DNA-directed RNA polymerase II subunit RPB3 |
| 67 | K1C19_HUMAN | 0.21 | 7.26E−04 | P08727 | KRT19 | Keratin, type I cytoskeletal 19 |
| 68 | PAK2_HUMAN | 0.20 | 7.46E−04 | Q13177 | PAK2 | PAK-2p34 |
| 69 | ZN593_HUMAN | 0.24 | 7.81E−04 | O00488 | ZNF593 | Zinc finger protein 593 |
| 70 | MYD88_HUMAN | 0.22 | 8.13E−04 | Q99836 | MYD88 | Myeloid differentiation primary response protein MYD88 |
| 71 | IL8_HUMAN | −0.23 | 9.48E−04 | P10145 | IL8 | IL-8 (7-77) |
| 72 | CUL2_HUMAN | −0.24 | 9.76E−04 | Q13617 | CUL2 | Cullin-2 |
| 73 | SEP15_HUMAN | −0.21 | 9.76E−04 | O60613 | SEP15 | 15 kDa selenoprotein |
| 74 | TNF13_HUMAN | −0.24 | 9.88E−04 | O75888 | TNFSF13 | Tumor necrosis factor ligand superfamily member 13 |
| 75 | APBA1_HUMAN | 0.25 | 1.03E−03 | Q02410 | APBA1 | Amyloid beta A4 precursor protein-binding family A member 1 |
| 76 | EPHB3_HUMAN | 0.21 | 1.03E−03 | P54753 | EPHB3 | Ephrin type-B receptor 3 |
| 77 | MK10_HUMAN | −0.18 | 1.05E−03 | P53779 | MAPK10 | Mitogen-activated protein kinase 10 |
| 78 | GDN_HUMAN | −0.26 | 1.17E−03 | P07093 | SERPINE2 | Glia-derived nexin |
| 79 | HMMR_HUMAN | −0.26 | 1.17E−03 | O75330 | HMMR | Hyaluronan mediated motility receptor |
| 80 | IL10_HUMAN | 0.22 | 1.17E−03 | P22301 | IL10 | Interleukin-10 |
| 81 | OLFM4_HUMAN | −0.23 | 1.19E−03 | Q6UX06 | OLFM4 | Olfactomedin-4 |
| 82 | CISY_HUMAN | −0.30 | 1.30E−03 | Q75390 | CS | Citrate synthase, mitochondrial |
| 83 | ID2_HUMAN | −0.28 | 1.30E−03 | Q02363 | ID2 | DNA-binding protein inhibitor ID-2 |
| 84 | MUTED_HUMAN | −0.29 | 1.35E−03 | Q8TDH9 | MUTED | Protein Muted homolog |
| 85 | SEPR_HUMAN | −0.25 | 1.42E−03 | Q12884 | FAP | Seprase |
| 86 | TR10A_HUMAN | −0.37 | 1.58E−03 | O00220 | TNFRSF10A | Tumor necrosis factor receptor superfamily member 10A |
| 87 | K2C8_HUMAN | −0.19 | 1.58E−03 | P05787 | KRT8 | Keratin, type II cytoskeletal 8 |
| 88 | TNFB_HUMAN | 0.20 | 1.58E−03 | P01374 | LTA | Lymphotoxin-alpha |
| 89 | ANFB_HUMAN | 0.19 | 1.58E−03 | P16860 | NPPB | BNP (5-32) |
| 90 | CP1B1_HUMAN | −0.30 | 1.72E−03 | Q16678 | CYP1B1 | Cytochrome P450 1B1 |
| 91 | BRPF3_HUMAN | −0.18 | 1.74E−03 | Q9ULD4 | BRPF3 | Bromodomain and PHD finger-containing protein 3 |
| 92 | AP4B1_HUMAN | −0.21 | 1.81E−03 | Q9Y6B7 | AP4B1 | AP-4 complex subunit beta-1 |
| 93 | GBRB1_HUMAN | −0.21 | 1.81E−03 | P18505 | GABRB1 | Gamma-aminobutyric acid receptor subunit beta-1 |
| 94 | SIA7F_HUMAN | 0.18 | 2.00E−03 | Q969X2 | ST6GALNAC6 | Alpha-N-acetylgalactosaminide alpha-2,6-sialyltransferase 6 |
| 95 | HXC11_HUMAN | −0.17 | 2.04E−03 | O43248 | HOXC11 | Homeobox protein Hox-C11 |
| 96 | PIGC_HUMAN | −0.15 | 2.05E−03 | Q92535 | PIGC | Phosphatidylinositol N-acetylglucosaminyltransferase subunit C |
| 97 | TRI22_HUMAN | −0.23 | 2.05E−03 | Q8IYM9 | TRIM22 | Tripartite motif-containing protein 22 |
| 98 | OSTP_HUMAN | −0.23 | 2.10E−03 | P10451 | SPP1 | Osteopontin |
| 99 | ZO2_HUMAN | 0.19 | 2.29E−03 | Q9UDY2 | TJP2 | Tight junction protein ZO-2 |
| 100 | PO2F1_HUMAN | −0.23 | 2.55E−03 | P14859 | POU2F1 | POU domain, class 2, transcription factor 1 |

TABLE 2

Up-regulated biomarker

| Nr | Uniprot Identifier | Log fold change | Adjusted p-value | Uniprot Accession | HGNC Symbol | Protein name |
|---|---|---|---|---|---|---|
| 1 | LMNA_HUMAN | 0.72 | 3.32E-09 | P02545 | LMNA | Lamin A, Prelamin-A/C, Lamin-A/C |
| 2 | YBOX1_HUMAN | 0.52 | 1.87E-08 | P67809 | YBX1 | Nuclease-sensitive element-binding protein 1 |
| 3 | JUN_HUMAN | 0.50 | 1.27E-07 | P05412 | JUN | Transcription factor AP-1 |
| 7 | AKT3_HUMAN | 0.48 | 2.47E-07 | Q9Y243 | AKT3 | RAC-gamma serine/threonine-protein kinase |
| 10 | YETS2_HUMAN | 0.32 | 5.28E-06 | Q9ULM3 | YEATS2 | YEATS domain-containing protein 2 |
| 15 | GRM1A_HUMAN | 0.27 | 1.10E-05 | Q96CP6 | GRAMD1A | GRAM domain-containing protein 1A |
| 16 | TPA_HUMAN | 0.23 | 1.14E-05 | P00750 | PLAT | Tissue-type plasminogen activator chain B |
| 18 | CADH1_HUMAN | 0.33 | 1.15E-05 | P12830 | CDH1 | E-Cad/CTF2 |
| 19 | LAMP2_HUMAN | 0.26 | 1.15E-05 | P13473 | LAMP2 | Lysosome-associated membrane glycoprotein 2 |
| 20 | LIFR_HUMAN | 0.30 | 2.17E-05 | P42702 | LIFR | Leukemia inhibitory factor receptor |
| 21 | TOP2A_HUMAN | 0.48 | 2.17E-05 | P11388 | TOP2A | DNA topoisomerase 2-alpha |
| 23 | NFAC4_HUMAN | 0.35 | 2.47E-05 | Q14934 | NFATC4 | Nuclear factor of activated T-cells, cytoplasmic 4 |
| 24 | SF3B3_HUMAN | 0.32 | 2.47E-05 | Q15393 | SF3B3 | Splicing factor 3B subunit 3 |
| 25 | UBIQ_HUMAN | 0.24 | 2.47E-05 | P62988 | UBC | Ubiquitin |
| 32 | MMP13_HUMAN | 0.25 | 6.32E-05 | P45452 | MMP13 | Collagenase 3 |
| 36 | NFKB1_HUMAN | 0.32 | 1.76E-04 | P19838 | NFKB1 | Nuclear factor NF-kappa-B p105 subunit |
| 39 | KLF5_HUMAN | 0.37 | 1.96E-04 | Q13887 | KLF5 | E-Krueppel-like factor 5 |
| 47 | B2LA1_HUMAN | 0.24 | 3.49E-04 | Q16548 | BCL2A1 | Bcl-2-related protein A1 |
| 49 | CASP3_HUMAN | 0.40 | 3.99E-04 | P42574 | CASP3 | Caspase-3 subunit p17 |
| 56 | SOX9_HUMAN | 0.23 | 4.39E-04 | P48436 | SOX9 | Transcription factor SOX-9 |
| 58 | MUC5B_HUMAN | 0.25 | 4.97E-04 | Q9HC84 | MUC5B | Mucin-5B |
| 62 | AQP1_HUMAN | 0.24 | 6.21E-04 | P29972 | AQP1 | Aquaporin-1 |
| 65 | GSHB_HUMAN | 0.17 | 6.35E-04 | P48637 | GSS | Glutathione synthetase |
| 67 | K1C19_HUMAN | 0.21 | 7.26E-04 | P08727 | KRT19 | Keratin, type I cytoskeletal 19 |
| 68 | PAK2_HUMAN | 0.20 | 7.46E-04 | Q13177 | PAK2 | PAK-2p34 |
| 69 | ZN593_HUMAN | 0.24 | 7.81E-04 | O00488 | ZNF593 | Zinc finger protein 593 |
| 70 | MYD88_HUMAN | 0.22 | 8.13E-04 | Q99836 | MYD88 | Myeloid differentiation primary response protein MyD88 |
| 75 | APBA1_HUMAN | 0.25 | 1.03E-03 | Q02410 | APBA1 | Amyloid beta A4 precursor protein-binding family A member 1 |
| 76 | EPHB3_HUMAN | 0.21 | 1.03E-03 | P54753 | EPHB3 | Ephrin type-B receptor 3 |
| 80 | IL10_HUMAN | 0.22 | 1.17E-03 | P22301 | IL10 | Interleukin-10 |
| 88 | TNFB_HUMAN | 0.20 | 1.58E-03 | P01374 | LTA | Lymphotoxin-alpha |
| 89 | ANFB_HUMAN | 0.19 | 1.58E-03 | P16860 | NPPB | BNP (5-32) |
| 94 | SIA7F_HUMAN | 0.18 | 2.00E-03 | Q969X2 | ST6GALNAC6 | Alpha-N-acetylgalactosaminide alpha-2,6-sialyltransferase 6 |
| 99 | ZO2_HUMAN | 0.19 | 2.29E-03 | Q9UDY2 | TJP2 | Tight junction protein ZO-2 |

TABLE 3

Down-regulated biomarker

| Nr | Uniprot Identifier | Log fold change | Adjusted p-value | Uniprot Accession | HGNC Symbol | Protein name |
|---|---|---|---|---|---|---|
| 4 | PABP1_HUMAN | -0.36 | 2.13E-07 | P11940 | PABPC1 | Polyadenylate-binding protein 1 |
| 5 | SMAD3_HUMAN | -0.59 | 2.13E-07 | P84022 | SMAD3 | Mothers against decapentaplegic homolog 3 |
| 6 | TIA1_HUMAN | -0.39 | 2.13E-07 | P31483 | TIA1 | Nucleolysin TIA-1 isoform p40 |
| 8 | CDN1A_HUMAN | -0.52 | 3.38E-07 | P38936 | CDKN1A | Cyclin-dependent kinase inhibitor 1 |
| 9 | LYAM1_HUMAN | -0.52 | 9.62E-07 | P14151 | SELL | L-selectin |
| 11 | AKTIP_HUMAN | -0.35 | 5.38E-06 | Q9H8T0 | AKTIP | AKT-interacting protein |
| 12 | HSP7C_HUMAN | -0.34 | 1.04E-05 | P11142 | HSPA8 | Heat shock cognate 71 kDa protein |
| 13 | PRI1_HUMAN | -0.36 | 1.04E-05 | P49642 | PRIM1 | DNA primase small subunit |
| 14 | RSSA_HUMAN | -0.35 | 1.07E-05 | P08865 | RPSA | 40S ribosomal protein SA |
| 17 | ZBT17_HUMAN | -0.55 | 1.14E-05 | Q13105 | ZBTB17 | Zinc finger and BTB domain-containing protein 17 |
| 22 | SPS2L_HUMAN | -0.23 | 2.20E-05 | Q9NUQ6 | SPATS2L | SPATS2-like protein |
| 26 | 2DMB_HUMAN | -0.35 | 3.41E-05 | P28068 | HLA-DMB | HLA class II histocompatibility antigen, DM beta chain |
| 27 | FAK1_HUMAN | -0.36 | 3.93E-05 | Q05397 | PTK2 | Focal adhesion kinase 1 |
| 28 | IFNG_HUMAN | -0.46 | 3.95E-05 | P01579 | IFNG | Interferon gamma |
| 29 | SP1_HUMAN | -0.36 | 4.14E-05 | P08047 | SP1 | Transcription factor Sp1 |
| 30 | ACTN1_HUMAN | -0.36 | 4.31E-05 | P12814 | ACTN1 | Alpha-actinin-1 |
| 31 | TIE1_HUMAN | -0.30 | 6.17E-05 | P35590 | TIE1 | Tyrosine-protein kinase receptor Tie-1 |
| 33 | TIMP1_HUMAN | -0.33 | 6.32E-05 | P01033 | TIMP1 | Metalloproteinase inhibitor 1 |
| 34 | VTNC_HUMAN | -0.51 | 6.76E-05 | P04004 | VTN | Somatomedin-B |
| 35 | K1C17_HUMAN | -0.20 | 1.70E-04 | Q04695 | KRT17 | Keratin, type I cytoskeletal 17 |
| 37 | NAP1_HUMAN | -0.27 | 1.91E-04 | Q9BU70 | C9orf156 | Nef-associated protein 1 |
| 38 | RL10_HUMAN | -0.28 | 1.91E-04 | P27635 | RPL10 | 60S ribosomal protein L10 |
| 40 | MMP1_HUMAN | -0.26 | 2.27E-04 | P03956 | MMP1 | 27 kDa interstitial collagenase |
| 41 | CDKN3_HUMAN | -0.33 | 2.36E-04 | Q16667 | CDKN3 | Cyclin-dependent kinase inhibitor 3 |
| 42 | CD59_HUMAN | -0.33 | 2.56E-04 | P13987 | CD59 | CD59 glycoprotein |
| 43 | PO2F2_HUMAN | -0.35 | 2.56E-04 | P09086 | POU2F2 | POU domain, class 2, transcription factor 2 |
| 44 | MPIP2_HUMAN | -0.28 | 2.76E-04 | P30305 | CDC25B | M-phase inducer phosphatase 2 |

TABLE 3-continued

Down-regulated biomarker

| Nr | Uniprot Identifier | Log fold change | Adjusted p-value | Uniprot Accession | HGNC Symbol | Protein name |
|---|---|---|---|---|---|---|
| 45 | FRAP_HUMAN | −0.27 | 2.78E−04 | P42345 | FRAP1 | Serine/threonine-protein kinase mTOR |
| 46 | IRS2_HUMAN | −0.33 | 3.10E−04 | Q9Y4H2 | IRS2 | Insulin receptor substrate 2 |
| 48 | ERBB2_HUMAN | −0.24 | 3.65E−04 | P04626 | ERBB2 | Receptor tyrosine-protein kinase erbB-2 |
| 50 | FINC_HUMAN | −0.31 | 3.99E−04 | P02751 | FN1 | Ugl-Y2 |
| 51 | LAC_HUMAN | −0.26 | 4.00E−04 | P01842 | IGLC3 | Ig lambda chain C regions |
| 52 | AURKB_HUMAN | −0.33 | 4.05E−04 | Q96GD4 | AURKB | Serine/threonine-protein kinase 12 |
| 53 | MPP3_HUMAN | −0.21 | 4.10E−04 | Q13368 | MPP3 | MAGUK p55 subfamily member 3 |
| 54 | CD2A2_HUMAN | −0.32 | 4.34E−04 | Q8N726 | CDKN2A | Cyclin-dependent kinase inhibitor 2A, isoform 4 |
| 55 | EPCAM_HUMAN | −0.30 | 4.39E−04 | P16422 | EPCAM | Epithelial cell adhesion molecule |
| 57 | TSP3_HUMAN | −0.24 | 4.39E−04 | P49746 | THBS3 | Thrombospondin-3 |
| 59 | CP3A7_HUMAN | −0.23 | 5.54E−04 | P24462 | CYP3A7 | Cytochrome P450 3A7 |
| 60 | NMDE3_HUMAN | −0.27 | 5.62E−04 | Q14957 | GRIN2C | Glutamate [NMDA] receptor subunit epsilon-3 |
| 61 | THYG_HUMAN | −0.34 | 5.62E−04 | P01266 | TG | Thyroglobulin |
| 63 | IL15_HUMAN | −0.80 | 6.21E−04 | P40933 | IL15 | Interleukin-15 |
| 64 | LAT1_HUMAN | −0.24 | 6.21E−04 | Q01650 | SLC7A5 | Large neutral amino acids transporter small subunit 1 |
| 66 | RPB3_HUMAN | −0.23 | 6.58E−04 | P19387 | POLR2C | DNA-directed RNA polymerase II subunit RPB3 |
| 71 | IL8_HUMAN | −0.23 | 9.48E−04 | P10145 | IL8 | IL-8 (7-77) |
| 72 | CUL2_HUMAN | −0.24 | 9.76E−04 | Q13617 | CUL2 | Cullin-2 |
| 73 | SEP15_HUMAN | −0.21 | 9.76E−04 | O60613 | SEP15 | 15 kDa selenoprotein |
| 74 | TNF13_HUMAN | −0.24 | 9.88E−04 | O75888 | TNFSF13 | Tumor necrosis factor ligand superfamily member 13 |
| 77 | MK10_HUMAN | −0.18 | 1.05E−03 | P53779 | MAPK10 | Mitogen-activated protein kinase 10 |
| 78 | GDN_HUMAN | −0.26 | 1.17E−03 | P07093 | SERPINE2 | Glia-derived nexin |
| 79 | HMMR_HUMAN | −0.26 | 1.17E−03 | O75330 | HMMR | Hyaluronan mediated motility receptor |
| 81 | OLFM4_HUMAN | −0.23 | 1.19E−03 | Q6UX06 | OLFM4 | Olfactomedin-4 |
| 82 | CISY_HUMAN | −0.30 | 1.30E−03 | O75390 | CS | Citrate synthase, mitochondrial |
| 83 | ID2_HUMAN | −0.28 | 1.30E−03 | Q02363 | ID2 | DNA-binding protein inhibitor ID-2 |
| 84 | MUTED_HUMAN | −0.29 | 1.35E−03 | Q8TDH9 | MUTED | Protein Muted homolog |
| 85 | SEPR_HUMAN | −0.25 | 1.42E−03 | Q12884 | FAP | Seprase |
| 86 | TR10A_HUMAN | −0.37 | 1.58E−03 | O00220 | TNFRSF10A | Tumor necrosis factor receptor superfamily member 10A |
| 87 | K2C8_HUMAN | −0.19 | 1.58E−03 | P05787 | KRT8 | Keratin, type II cytoskeletal 8 |
| 90 | CP1B1_HUMAN | −0.30 | 1.72E−03 | Q16678 | CYP1B1 | Cytochrome P450 1B1 |
| 91 | BRPF3_HUMAN | −0.18 | 1.74E−03 | Q9ULD4 | BRPF3 | Bromodomain and PHD finger-containing protein 3 |
| 92 | AP4B1_HUMAN | −0.21 | 1.81E−03 | Q9Y6B7 | AP4B1 | AP-4 complex subunit beta-1 |
| 93 | GBRB1_HUMAN | −0.21 | 1.81E−03 | P18505 | GABRB1 | Gamma-aminobutyric acid receptor subunit beta-1 |
| 95 | HXC11_HUMAN | −0.17 | 2.04E−03 | O43248 | HOXC11 | Homeobox protein Hox-C11 |
| 96 | PIGC_HUMAN | −0.15 | 2.05E−03 | Q92535 | PIGC | Phosphatidylinositol N-acetylglucosaminyltransferase subunit C |
| 97 | TRI22_HUMAN | −0.23 | 2.05E−03 | Q8IYM9 | TRIM22 | Tripartite motif-containing protein 22 |
| 98 | OSTP_HUMAN | −0.23 | 2.10E−03 | P10451 | SPP1 | Osteopontin |
| 100 | PO2F1_HUMAN | −0.23 | 2.55E−03 | P14859 | POU2F1 | POU domain, class 2, transcription factor 1 |

EXAMPLE 2

Classification Test

In addition, for the data multivariate classification rules were constructed for discriminating between recurrent and non-recurrent samples. Multivariate classifiers were built by applying the nearest shrunken centroid classification method called Prediction Analysis of Microarrays (PAM) which selects from the full data set a subset of proteins capable of discriminating between the classes based on their joint expression profiles (Tibshirani R. et al., PNAS 99(10):6567-72.). Optimal PAM threshold parameters were determined in an internal cross-validation step, while the misclassification errors of the classifiers were estimated by an outer 0.632 bootstrap loop incorporating 100 bootstrap samples.

This analysis led to an optimal discrimination of the sample types with a classificator based on the expression of the proteins LMNA, YBOX1, JUN, AKT3, SMAD3, LYAM1, PABP1, TIA1, CASP3, CDN1A, CASP9, YETS2, PO2F2, TOP2A, RSSA, NFAC4, ZBT17, AKTIP, HSP7C, and LIFR. The proteins are ordered by their selection frequency in the different bootstrap samples.

With the classificator described above the following classification of the sample set described in example 1 was obtained:

| | | Classified as | |
|---|---|---|---|
| | | Non-Recurrent | Recurrent |
| Sample type | Non-Recurrent (n = 6) | 6 | 0 |
| | Recurrent (n = 19) | 2 | 17 |

This corresponds to a sensitivity of 81% at a specificity of 100% for the prediction of recurrence. The overall accuracy of the classification is 91%.

The proteins chosen for the classification match the proteins of highest significance in the statistical LIMMA analysis of example 1 and provided in the tables 1-3.

Besides of the complex algorithm, also a hierarchical clustering based on the proteins selected by PAM resulted in a good separation of the two groups (not shown).

In addition, we build a Random Forest classifier based on the 20 most differentially regulated proteins from the LIMMA analysis. For a classification on the training set all samples were classified correct, corresponding to a sensitivity of 100% and a specificity of 100%. To assess the transferability to other test sets, we performed a leave-one-out cross validation. The classification results for the different test sets in the cross validation steps are summarized as a receiver operator curve (FIG. 1). The respective overall misclassification rate for the cross validation was as low as 20% (SD 0.08) with an area under the curve of 90.4%.

The invention claimed is:

1. A method for predicting the risk of recurrence of bladder cancer in a subject who has had a tumor removed by surgery, comprising:
   (a) determining, by immunoassay, the amounts of protein biomarkers in a tumor tissue sample from the subject who has had a tumor removed by surgery, wherein the protein biomarkers comprise Lamin A ("LMNA") and Nuclease-sensitive element-binding protein 1 ("YBX1"), wherein the immunoassay comprises:
      (i) contacting the sample with an antibody microarray comprising antibodies that recognize LMNA protein and antibodies that recognize YBX1; and
      (ii) measuring the amounts of bound protein biomarkers and thereby determining the amounts of the protein biomarkers present in the sample;
   (b) comparing the amounts of the protein biomarkers with a reference amount for the protein biomarkers, wherein the reference amount is derived from a subject or group of subjects known to be at risk for recurrence of bladder cancer, or from a subject or group of subjects known to not be at risk for recurrence of bladder cancer;
   (c) diagnosing the subject as at risk of recurrence of bladder cancer if the amounts of protein biomarkers are increased as compared to the reference amounts; and
   (d) treating the subject, who is at risk of recurrence of bladder cancer, with an anti-bladder cancer treatment.

2. The method of claim 1, wherein the protein biomarkers further comprise at least one additional protein biomarker selected from the group consisting of Transcription factor AP-1 ("JUN"), RAC-gamma serine/threonine-protein kinase("AKT3"), YEATS domain-containing protein 2 ("YEATS2"), GRAM domain-containing protein 1A ("GRAMD1A"), Tissue-type plasminogen activator chain B ("PLAT"), E-Cad/CTF2 ("CDH1"), Lysosome-associated membrane glycoprotein 2 ("LAMP2"), Leukemia inhibitory factor receptor ("LIFR"), DNA topoisomerase 2-alpha ("TOP2A"), Nuclear factor of activated T-cells, cytoplasmic 4 ("NFATC4"), Splicing factor 3B subunit 3 ("SF3B3"), Ubiquitin ("UBC"), Collagenase 3 ("MMP13"), Nuclear factor NF-kappa-B p105 subunit ("NFKB1"), Krueppel-like factor 5 ("KLF5"), Bcl-2-related protein A 1 ("BCL2A1"), Caspase-3 subunit p17 ("CASP3"), Transcription factor SOX-9 ("SOX9"), Mucin-5B ("MUC5B"), Aquaporin-1 ("AQP1"), Glutathione synthetase ("GSS"), Keratin, type I cytoskeletal 19 ("KRT19"), PAK-2p34 ("PAK2"), Zinc finger protein 593 ("ZNF593"), Myeloid differentiation primary response protein MyD88 ("MYD88"), Amyloid beta A4 precursor protein-binding family A member 1 ("APBA1"), Ephrin type-B receptor 3 ("EPHB3"), Interleukin-10 ("IL10"), Lymphotoxin-alpha ("LTA"), BNP(5-32) ("NPPB"), Alpha-N-acetylgalactosaminide alpha-2,6-sialyltransferase 6 ("ST6GALNAC6"), Tight junction protein ZO-2 ("TJP2"), and a combination thereof, and the subject is diagnosed as at risk of recurrence of bladder cancer if the amount of the at least one additional protein biomarker is increased as compared to the reference amount.

3. The method of claim 1, wherein the protein biomarkers further comprise at least one additional biomarker selected from the group consisting of PABPC1, SMAD3, TIA1, CDKN1A, SELL, AKTIP, HSPA8, PRIM1, RPSA, ZBTB17, SPATS2L, HLA-DMB, PTK2, IFNG, SP1, ACTN1, TIE1, TIMP1, VTN, KRT17, C9orf156, RPL10, MMP1, CDKN3, CD59, POU2F2, CDC25B, FRAP1, IRS2, ERBB2, FN1, IGLC3, AURKB, MPP3, CDKN2A, EPCAM, THBS3, CYP3A7, GRIN2C, TG, IL15, SLC7A5, POLR2C, IL8, CUL2, SEP15, TNFSF13, MAPK10, SERPINE2, HMMR, OLFM4, CS, ID2, MUTED, FAP, TNFRSF10A, KRT8, CYP1B1, BRPF3, AP4B1, GABRB1, HOXC11, PIGC, TRIM22, SPP1, and POU2F1; and the subject is diagnosed as at risk of recurrence of bladder cancer if the amount of the at least one additional biomarker is decreased as compared to the reference amount.

4. The method of claim 1, wherein the surgery is transurethral resection, radical cystectorny, or partial eystectomy.

5. The method of claim 1, further comprising determination of the level of at least one protein biomarker selected from the group consisting of AKT3, TOP2A, YETS2, Nucleolysin TIA-1 isoform p40 ("TIA1"), Cyclin-dependent kinase inhibitor 1("CDKN1A"), Mothers against decapentaplegic homolog 3 ("SMAD3"), and Polyadenylate-binding protein 1("PABP1").

6. The method of claim 1, wherein the antibody is an antibody or functional fragment thereof and wherein the antibody or functional fragment thereof further comprises a detectable label.

7. The method of claim 1, wherein the antibody is an antibody or functional fragment thereof, and wherein the amount of the biomarker is measured by obtaining signal from the antibody or the functional fragment thereof.

8. The method of claim 1, wherein the protein biomarkers further comprise one or more biomarkers selected from the group consisting of Polyadenylate-binding protein 1 ("PABPC1"), SMAD3, TIA1, AKT3, CDKN1A, L-selectin ("SELL"), YEATS2, AKT-interacting protein ("AKTIP"), Heat shock cognate 71 kDa protein ("HSPA8"), DNA primase small subunit ("PRIM1"), 40S ribosomal protein SA ("RPSA"), GRAMD1A, PLAT, Zinc finger and BTB domain-containing protein 17 ("ZBTB17"), CDH1, LAMP2, LIFR, TOP2A, SPATS2-like protein ("SPATS2L"), NFATC4, SF3B3, UBC, HLA class II histocompatibility antigen, DM beta chain ("HLA-DMB"), Focal adhesion kinase 1 ("PTK2"), Interferon gamma ("IFNG"), Transcription factor Sp1 ("SP1"), Alpha-actinin-1("ACTN1"), Tyrosine-protein kinase receptor Tie-1 ("TIE1"), MMP13, Metalloproteinase inhibitor 1 ("TIMP1"), Somatomedin-B ("VTN"), Keratin, type I cytoskeletal 17 ("KRT17"), NFKB1, Net-associated protein 1 ("C9orf156"), 60S ribosomal protein L10 ("RPL10"), KLF5, 27 kDa interstitial collagenase ("MMP1"), Cyclin-dependent kinase inhibitor 3 ("CDKN3"), CD59 glycoprotein ("CD59"), POU domain, class 2, transcription factor 2 ("POU2F2"), M-phase inducer phosphatase 2 ("CDC25B"), Serine/threonine-protein kinase mTOR ("FRAP1"), Insulin receptor substrate 2 ("IRS2"), BCL2A1, Receptor tyrosine-protein kinase erbB-2 ("ERBB2"), CASP3, Ug1-Y2 ("FN1"), Ig lambda chain C regions ("IGLC3"), Serine/threonine-protein kinase 12 ("AURKB"), MAGUK p55 subfamily member 3 ("MPP3"), Cyclin-dependent kinase inhibitor 2A, isoform 4 ("CDKN2A"), Epithelial cell adhesion molecule ("EPCAM"), SOX9, Thrombospondin-3 ("THBS3"), MUC5B, Cytochrome P450 3A7 ("CYP3A7"), Glutamate receptor subunit epsilon-3 ("GRIN2C"), Thyroglobulin ("TG"), AQP1, Interleukin-15 ("IL15"), Large neutral amino acids transporter small subunit 1 ("SLC7A5"), GSS, ("POLR2C"), KRT19, PAK2, ZNF593, MYD88, Interleukin-8 "IL8"), Cullin-2 ("CUL2"), 15 kDa selenoprotein ("SEP15"), Tumor necrosis factor ligand superfamily member 13 ("TNFSF13"), APBA1, EPHB3, Mitogen-activated protein kinase 10 ("MAPK10"), Glia-derived nexin ("SERPINE2"), Hyaluronan mediated motility receptor ("HMMR"), IL10, Olfactomedin-4 ("OLFM4"), Citrate synthase, mitochondrial ("CS"), DNA-binding protein inhibitor ID-2 ("ID2"), Protein Muted homolog ("MUTED"), Seprase ("FAP"), Tumor necrosis factor receptor superfamily member 10A ("TNFRSF10A"), Keratin, type II cytoskeletal 8 ("KRT8"), LTA, NPPB, Cytochrome P450 1B1 ("CYP1B1"), Bromodomain and PHD finger-containing protein 3("BRPF3"), AP-4 complex subunit beta-1 ("AP4B1"), Gamma-aminobutyric acid receptor subunit beta-1 ("GABRB1"), ST6GALNAC6, Homeobox protein Hox-C11 ("HOXC11"), Phosphatidylinositol N-acetylglucosaminyltransferase subunit C ("PIGC"), Tripartite motif-containing protein 22 ("TRIM22"), Osteopontin ("SPP1"), TJP2, and POU domain, class 2, transcription factor 1 ("POU2F 1").

9. The method of claim 1, further comprising monitoring progression of bladder cancer in the subject who is at risk of bladder cancer recurrence.

\* \* \* \* \*